United States Patent
Kuo et al.

(10) Patent No.: US 9,266,813 B2
(45) Date of Patent: Feb. 23, 2016

(54) STILBENOID COMPOUND AS INHIBITOR FOR SQUAMOUS CARCINOMA AND HEPATOMA AND USES THEREOF

(71) Applicant: AnnCare Bio-Tech Center Inc., Taichung (TW)

(72) Inventors: Sheng-Chu Kuo, Taichung (TW); Jai-Sing Yang, Taichung (TW); Min-Tsang Hsieh, Taichung (TW); Tian-Shung Wu, Taichung (TW); Kuo-Hsiung Lee, Taichung (TW); Huei-Wen Chen, Taichung (TW); Li-Jiau Huang, Taichung (TW); Hsin-Yi Hung, Taichung (TW); Tzong-Der Way, Taichung (TW); Ling-Chu Chang, Taichung (TW); Hui-Yi Lin, Taichung (TW); Yung-Yi Cheng, Taichung (TW); Chin-Yu Liu, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 14/229,339

(22) Filed: Mar. 28, 2014

(65) Prior Publication Data

US 2014/0303241 A1    Oct. 9, 2014

Related U.S. Application Data

(60) Provisional application No. 61/807,837, filed on Apr. 3, 2013.

(51) Int. Cl.
| | | |
|---|---|---|
| *A01N 43/32* | (2006.01) |
| *A61K 31/335* | (2006.01) |
| *C07D 319/06* | (2006.01) |
| *C07C 69/00* | (2006.01) |
| *C07C 69/712* | (2006.01) |
| *C07C 69/675* | (2006.01) |
| *C07C 67/30* | (2006.01) |
| *C07D 407/04* | (2006.01) |

(52) U.S. Cl.
CPC .............. *C07C 69/712* (2013.01); *C07C 67/30* (2013.01); *C07C 69/675* (2013.01); *C07D 319/06* (2013.01); *C07D 407/04* (2013.01)

(58) Field of Classification Search
CPC .. C07D 319/06; C07D 319/20; C07D 493/08; C07D 319/08; A61K 31/357
USPC .................... 514/452, 546; 549/448; 560/144
See application file for complete search history.

(56) References Cited

FOREIGN PATENT DOCUMENTS

CN         1807404 A   *  7/2006

OTHER PUBLICATIONS

Cardile, V., L. Lombardo, C. Spatafora, C. Tringali "Chemo-enzymatic synthesis and cell-growth inhibition activity of resveratrol analogues" Biorganic Chemistry (2005), Oct. 1, 2004, 33: pp. 22-33.*

Sun, B., J. Hoshino, K. Jermihov, L. Marler, J. Pezzuto, A. Mesecar, M. Cushman "Design, synthesis, and biological evaluation of resveratrol analogues as aromatase and quinone reductase 2 inhibitors for chemoprevention of cancer" Bioorganic and Medical Chemistry (2010), May 24, 2010, 18: pp. 5352-5366.*

* cited by examiner

*Primary Examiner* — Alicia L Otton
*Assistant Examiner* — Sagar Patel
(74) *Attorney, Agent, or Firm* — WPAT, P.C.; Anthony King

(57) ABSTRACT

The present invention provides a series of derivatives of stilbenoid which are useful as new inhibitory agents against head and neck squamous cell carcinoma (HNSCC) and hepatoma.

7 Claims, 7 Drawing Sheets
(3 of 7 Drawing Sheet(s) Filed in Color)

STILBENOID COMPOUND AS INHIBITOR FOR SQUAMOUS CARCINOMA AND HEPATOMA AND USES THEREOF

CROSS-REFERENCES TO RELATED APPLICATIONS

This application claims priority to U.S. Priority Patent Application No. 61/807,837 filed on 3 Apr. 2013. All disclosure of which is incorporated herein by reference in its entirety.

BACKGROUND OF THE INVENTION

1. Field of the Invention

The present invention is related to stilbenoid compounds as inhibitors for squamous carcinoma and hepatoma and the uses thereof. More specifically, the present invention is related to compounds capable of inhibiting the cell viability and proliferation of squamous cell carcinoma and hepatocellular carcinoma, the pharmaceutical compositions of said compounds, the method for treating cancer using said compounds, and the method of manufacture of said compounds.

2. The Prior Arts

Head and neck cancer is the sixth most common cancer worldwide and accounts for 6% of all cancer cases. However, it ranks the fourth most commonly occurred cancer in Taiwan. Head and neck cancer is a broad term of epithelial malignancies that occurred in the paranasal sinuses, nasal cavity, oral cavity, pharynx and larynx. Approximately 95% of histological type is squamous cell carcinoma (HNSCC), while others are salivary gland tumors, lymphomas and sarcomas. Nowadays, several risk factors related to HNSCC onset were identified. The most important risk factors in HNSCC are from tobacco and alcohol consumption. Other risk factors include inhalant industrial exposures, human papilloma virus (HPV) infection and Epstein-Barr virus (EBV) infection. Despite improvement in the therapy of HNSCC, patients still suffer from a very poor prognosis following progression after standard therapy regimens. Due to high recurrence and metastasis property, the survival rate of most of the patients is very low.

Currently, there are three main treatments for management of HNSCC, which are radiation therapy, surgery and chemotherapy. The primary treatments are radiation and surgery or both in combination of adjuvant treatment of chemotherapy. The optimal combination of treatments is dependent on the cancer sites and disease stages. Moreover, the most common drugs used in combination with radiation therapy, so called chemoradiation, are cisplatin (Market available brands: Platinol, Platinol-AQ), fluorouracil (Market available brands: Adrucil, Efudex, Fluoroplex) and cetuximab (Market available brand: Erbitux). Other chemotherapy drugs used include carboplatin (Market available brand: Paraplatin), docetaxel (Market available brand: Taxotere) and gemcitabine, paclitaxel (Market available brand: Taxol), methotrexate (Market available brands: Abitrexate, Folex, Folex PFS, Mexate, Mexate-AQ) and bleomycin (Market available brands Blenoxane).

In spite of their antitumor activities, a lot of side effects come with chemotherapy. The difficulties of side effects include high infection risk, bruising, anemia, nausea, vomiting, sore mouth, hearing loss, fatigue and hair loss, which bother HNSCC patients. Clinical observations have found that cisplatin can cause renal failure and cytotoxicity. Both cisplatin and taxanes can result in toxicities, including haematological toxicity, neurotoxicity, nephrotoxicity and ototoxicity. Fluorouracil, methotrexate and taxanes may induce mucosal cytotoxicity that worsens the outcome after radiation therapy. So far, cisplatin-based chemotherapy is the most widely used treatment in HNSCC because of its superior survival benefits. However, there are limitations for the chemotherapy of cisplatin such as the high occurrence of drug resistance and the severe toxicity due to high dosage. An ideal HNSCC chemotherapy drug, which can be effective in antitumor activity while avoiding the recurrence and metastasis of HNSCC, should have low cytotoxicity and low side effects.

Hepatocellular carcinoma (HCC) is the fifth most common malignancy in the world and the second most common cause for cancer-related death. It was more prevalent in Asia and Africa; however, it is now showing a rising incidence among Western countries. HCC, which is an aggressive tumor, frequently occurs in the setting of chronic liver diseases and cirrhosis. The major risk factors related to HCC include infections with hepatitis B virus (HBV) or hepatitis C virus (HCV), alcoholic liver diseases, and non-alcoholic fatty liver diseases. In western countries, type II diabetes and obesity are the two emerging causes of HCC. Clinically, HCC is often diagnosed late and shows extremely poor prognosis after standard therapy regimens as well as very low survival rate.

Currently, several treatment modalities are available for HCC, including surgical intervention (tumor resection and liver transplantation), percutaneous interventions (ethanol or acetic acid injection, radiofrequency thermal ablation, microwave ablation and cryoablation), transarterial interventions (embolization, chemoperfusion, or chemoembolization), systematic chemotherapy and molecularly target therapies. Drugs used in systemic chemotherapy can be categorized into cytotoxic drugs and molecular target drugs. Cytotoxic drugs includes Xeloda (capecitabine), Etoposide, Irinotecan, 5-Fu, Doxorubicin, Mitoxantrone, and Thymitaq (Nolatrexed), which exhibit powerful side effects and high occurrence of drug resistance. Molecular target drugs include Nexavar (sorafenib), Sutent (sunitinib), and Avastin (bevacizumab), etc, which also show high occurrence of drug resistance. Side effects by chemotherapy not only affect the quality of living of patients of HCC but also lower the survival rates.

The development of new drugs that are effective against HCC with low toxicity is one important task in the medical and pharmaceutical field. To conquer the side effects and reduce the morbidity and mortality of HCC at the same time, the development of novel systemic chemotherapy for advanced HCC treatment is of principal importance. The ideal chemotherapeutic drugs must possess antitumor properties with high efficacy and a very low cytotoxicity for patients.

Resveratrol (3,5,4'-trihydroxy-trans-stilbene) is a stilbenoid, a type of natural phenol, and a phytoalexin. In 1939, Michio Takaoka first reported resveratrol isolated from the poisonous but medicinal *Veratrum album*, a variety of grandiflorum, in a Japanese article. Resveratrol is found in the skin of red grapes and in other fruits as well as in the roots of Japanese knotweed (*Polygonum cuspidatum*). The pharmacological effects of resveratrol include life extension, cardioprotective effects, antidiabetes, and anti-inflammatory effects. Besides, resveratrol shows anti-cancer effects in animal models. However, this pharmaceutical anti-cancer effect is restricted due to low bioavailability.

No marked toxicity of resveratrol were observed in the group of rat received 0.3 g/kg/day for 4 weeks. Previous studies had discussed the adverse effects of resveratrol which 104 patients (including placebo) had been tested. The highest doses were 5 g/70 kg for a single intake and 0.9 g/day for iterative administration. No serious adverse event was detected in any of these studies. Adverse events were mild and only lasted for a few days.

Pterostilbene is a natural phenolic stilbenoid which is a phytoalexin. Pterostilbene could be found in grapes, a variety of berries and medicinal plants. The pharmacological effects of pterostilbene are antimicrobial, antioxidant, anti-inflammatory, hypolipidemic, antidiabetic activities, and memory improvement. The side effects and toxicity of pterostilbene are very low. The results of 28 days subchronic toxicity study indicated that at dose up to 3.0 g/kg/day, no significant adverse biochemical parameters and toxic effects were noted.

SUMMARY OF THE INVENTION

As a result, the present invention provides a compound of Formula I:

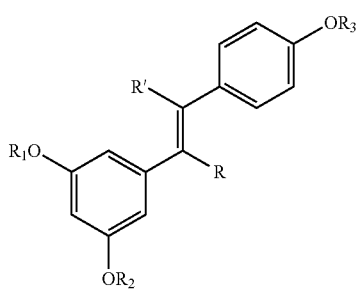

I or a stereoisomer, a geometric isomer, a tautomer, an N-oxide, a hydrate, a solvate, a metabolite or a pharmaceutically acceptable salt or prodrug thereof,
wherein R', R is hydrogen or $C_{1-3}$ alkyl; $R_1$, $R_2$, $R_3$ are each, independently, hydrogen, $C_{1-3}$ alkyl,

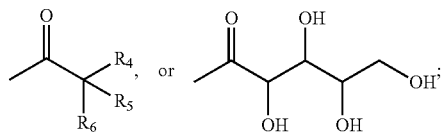

$R_4$, $R_5$, $R_6$ are each, independently, hydrogen, $C_{1-3}$ alkyl, $(CH_2)_n$—$CH_2OH$, or $(CHOH)_n$—$CH_2OH$ (n=0-3); and at least one of $R_1$, $R_2$, $R_3$ is

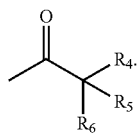

In some embodiments of the present invention, when $R_1$, $R_2$, $R_3$ are each, independently.

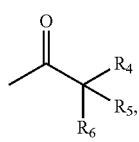

at least one of $R_4$, $R_5$, $R_6$ is $(CH_2)_n$—$CH_2OH$, n=0 to 3; in some embodiments of the present invention, when $R_1$, $R_2$, $R_3$ are

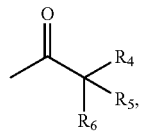

at least one of $R_4$, $R_5$, $R_6$ is $(CHOH)_n$—$CH_2OH$, n=0 to 3.

Another aspect of the present invention is to provide a pharmaceutical composition comprising the compound of Formula I. The pharmaceutical composition of the present invention further comprises a pharmaceutically acceptable carrier, excipient, diluent, adjuvant, medium, or combinations thereof.

Another aspect of the present invention is to provide a method for treating squamous carcinoma/hepatoma in a subject in need thereof, the method comprising administrating to said subject an therapeutically effective amount of the compound of Formula I.

Another aspect of the present invention is to provide a method for manufacture of compound of Formula I, comprising deprotecting a compound of Formula II:

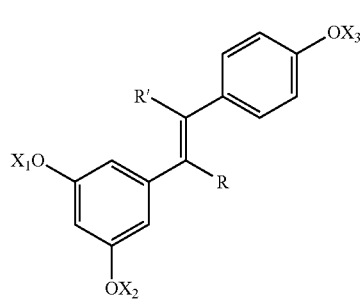

II wherein, R', R is hydrogen or $C_{1-3}$ alkyl; $X_1$, $X_2$, $X_3$ are each, independently, hydrogen, $C_{1-3}$ alkyl, or

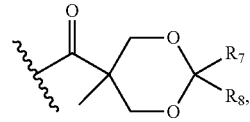

wherein $R_7$ and $R_8$ are each, independently, hydrogen or $C_{1-3}$ alkyl; $X_1$, $X_2$, $X_3$ are not all selected from hydrogen and $C_{1-3}$ alkyl, to form a compound of Formula I:

Formula I

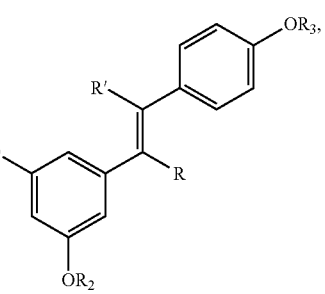

I wherein R', R is hydrogen or $C_{1-3}$ alkyl; $R_1$, $R_2$, $R_3$ are each, independently, hydrogen, $C_{1-3}$ alkyl,

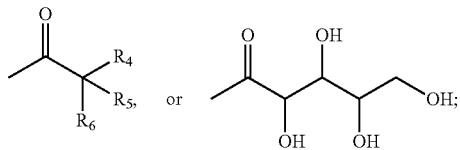

$R_4$, $R_5$, $R_6$ are each, independently, hydrogen, $C_{1-3}$ alkyl, $(CH_2)_n$—$CH_2OH$, or $(CHOH)_n$—$CH_2OH$, n=0 to 3; at least one of $R_1$, $R_2$, $R_3$ is

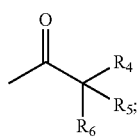

when $R_1$, $R_2$, $R_3$ are each, independently,

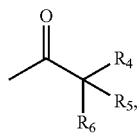

at least one of $R_4$, $R_5$, $R_6$ is $(CH_2)_n$—$CH_2OH$, n=0 to 3; and when $R_1$, $R_2$, $R_3$ are each, independently,

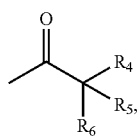

at least one of $R_4$, $R_5$, $R_6$ is $(CHOH)_n$—$CH_2OH$, n=0 to 3. In some embodiments of the present invention, the compound of Formula II is synthesized by reacting the compound of Formula III:

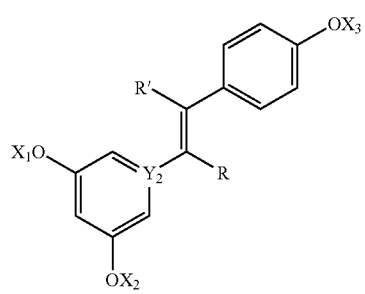

with the compound of Formula IV:

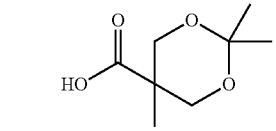

wherein R', R is hydrogen or $C_{1-3}$ alkyl; $Y_1$, $Y_2$, $Y_3$ are each, independently, hydrogen, or $C_{1-3}$ alkyl; and P is OH or Cl.

Another aspect of the present invention is to provide a compound of Formula II:

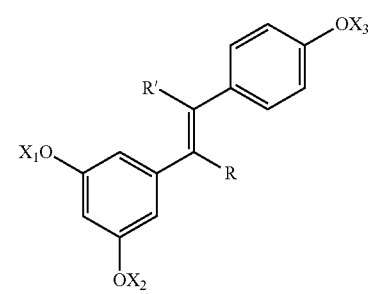

wherein, R', R is hydrogen or $C_{1-3}$ alkyl; $X_1$, $X_2$, $X_3$ are each, independently, hydrogen, $C_{1-3}$ alkyl, or $Y_3$

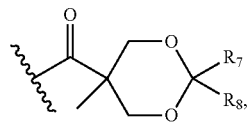

wherein $R_7$ and $R_8$ are each, independently, hydrogen or $C_{1-3}$ alkyl; $X_1$, $X_2$, $X_3$ are not all selected from hydrogen and $C_{1-3}$ alkyl.

The compounds of the present invention show potent anti-cancer activity with very low toxicity comparing to some of the drugs/compounds used in the prior art; besides, the high water solubility of the compounds of the present invention can further lead to high absorption rate in a subject, hence, is suitable and safe for the use in cancer treatment.

The present invention is further explained in the following embodiment, illustrations and examples. Those examples below should not, however, be considered to limit the scope of the invention, it is contemplated that modifications will readily occur to those skilled in the art, which modifications will be within the spirit of the invention and scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Definition and General Terminology

Figure 1:
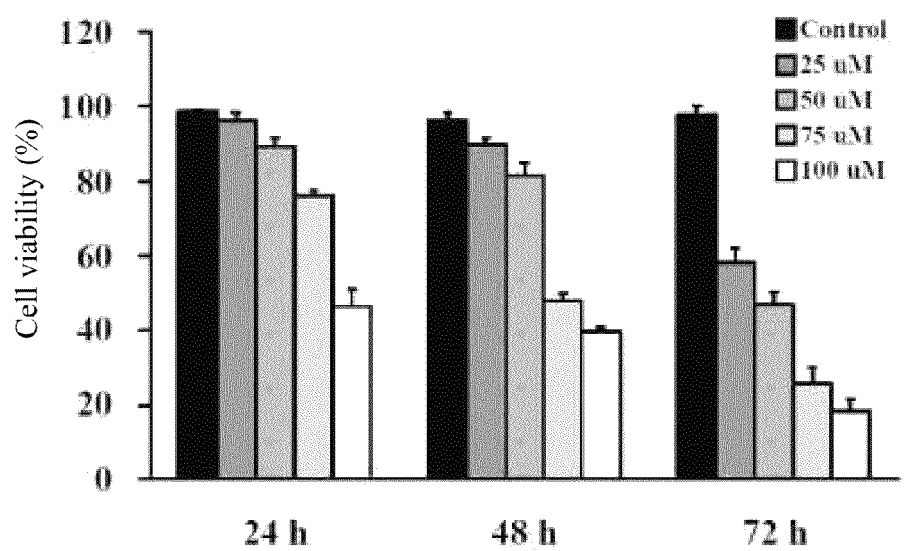
FIG. 1, effect of compound 2-4 on viability of cisplatin-resistant head and neck squamous carcinoma (CAR) cell.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "prodrug" refers to a compound that is transformed in vivo into a compound of formula (I). Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic $C_{1-24}$ esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., ed., *Bioreversible Carriers in Drug Design, American Pharmaceutical Association and Pergamon Press*, 1987; Rautio et al., Prodrugs: Design and Clinical Applications, *Nature Reviews Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the present invention includes metabolite of the compound of the invention, which includes the metabolite produced after contacting the compound of the invention with a mammal for a certain amount of time.

As used herein, a "pharmaceutically acceptable salt" refers to organic or inorganic salts of a compound of the invention. Pharmaceutically acceptable salts are well known in the art. For example, Berge et al., describe pharmaceutically acceptable salts in detail in *J. Pharmacol Sci*, 1977, 66, 1-19, which is incorporated herein by reference. Some non-limiting examples of pharmaceutically acceptable, nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. The pharmaceutically acceptable salt is an alkali metal salt, an alkaline earth metal salt, an ammonium salt or a $N^+(C_{1-4} alkyl)_4$ salt. This invention also envisions the quaternization of any basic nitrogen-containing groups of the compounds disclosed herein. Water or oil-soluble or dispersable products may be obtained by such quaternization. Representative alkali or alkaline earth metal salts include sodium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

The phrase "pharmaceutically acceptable" indicates that the compound, raw material, composition and/or dose must be compatible within a reasonable range of medical judgment and, when contacting with tissues of patients, is without overwhelming toxicity, irritation, transformation, or other problems and complications that are corresponsive to reasonable benefit/risk, while being effectively applicable for the predetermined purposes.

As used herein, the term "therapeutically effective amount" means the amount of a compound that, when administered to a mammal for treating a disease, is sufficient to effect such treatment for the disease. The "therapeutically-effective amount" will vary depending on the compound, the disease, and its severity and the age, weight, etc., of the mammal to be treated.

Synthesis of Compounds of the Invention

In general, the compounds of the invention are synthesized according to Scheme 1. As shown in Scheme 1, triphenolic compound (compound 1-1) and different equivalents of compound 1-2 were reacted in N,N-dimethylaminopyridine (DMAP) and were catalyzed by N,N-dicyclohexylcarbodiimide (DCC) to give diverse esters (compound 1-3 to compound 1-7) after coupling and purification. The esters obtained were then underwent deprotection in methanol with the presence of Lewis acid to give corresponding compounds (compound 1-8 to compound 1-9).

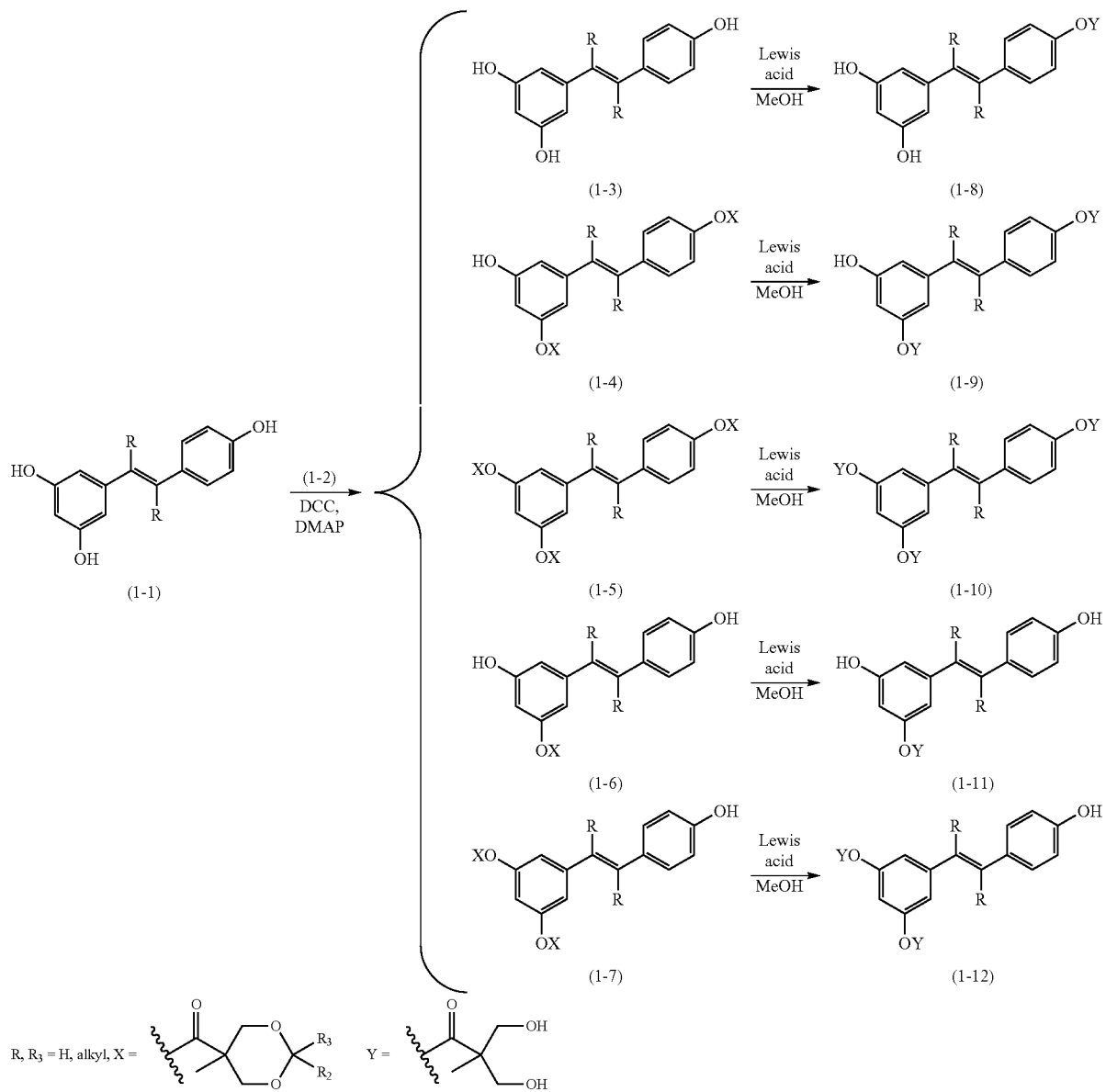
For the synthesis of compound 2-3 and compound 2-4, please refer to Scheme 2.
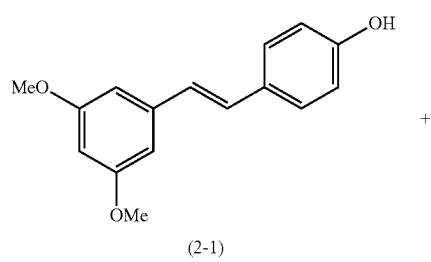
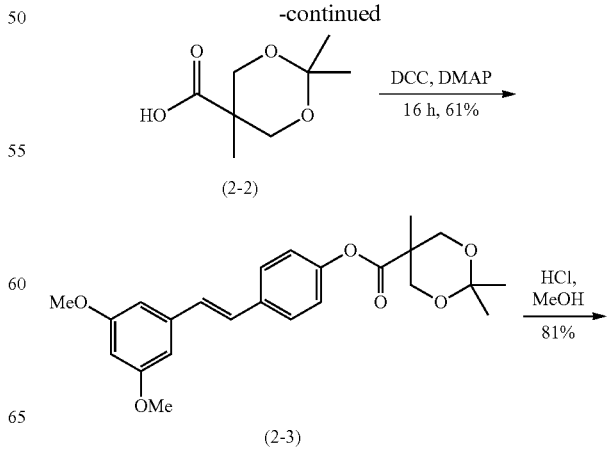

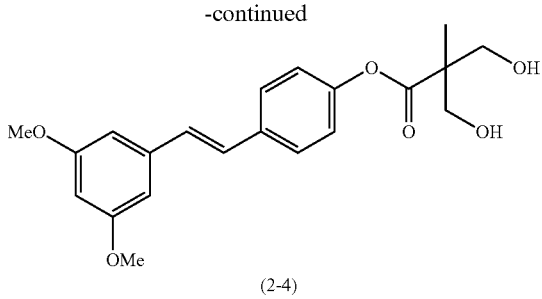

(2-4)

Example 1

Preparation of 4-(3,5-dimethoxystyryl)phenyl 2,2,5-trimethyl-1,3-dioxane-5-carboxylate (compound 2-3)

Please refer to Scheme 2. To a stirred solution of compound 2-2 (0.740 g, 4.25 mmol) in CH$_2$Cl$_2$ (25 mL), N,N-dicyclohexylcarbodiimide (DCC, 1.140 g, 5.53 mmol), compound 2-1 (1.090 g, 4.25 mmol) and N,N-dimethylaminopyridine, (DMAP, 0.052 g, 0.43 mmol) was added sequentially at room temperature. The reaction mixture was stirred at the same temperature for 18 hours and then H$_2$O (15 mL) was added to quench the reaction. The aqueous layer was separated and extracted with CH$_2$Cl$_2$ (2×20 mL). The combined organic extracts were washed with brine, dried over MgSO$_4$, filtered and concentrated to give the crude product, which was then purified by flash chromatography on silical gel with EtOAc/n-hexane (1:2) to afford compound 2-3 (1.070 g, 61% yield) as white solid.

$^1$H NMR (CDCl$_3$, 200 MHz): δ 7.49 (d, J=8.6 Hz, 2H), 7.09-6.99 (m, 4H), 6.65-6.63 (m, 2H), 6.38 (s, 1H), 4.21 (d, J=11.8 Hz, 2H), 3.80 (s, 6H), 3.75 (d, J=11.8 Hz, 2H), 1.46 (s, 3H), 1.43 (s, 3H), 1.33 (s, 3H); $^{13}$C NMR (CDCl$_3$, 50 MHz): δ172.7, 160.7, 150.1, 139.1, 134.5, 129.0, 128.0, 127.4, 121.7, 104.5, 100.1, 97.0, 66.0, 55.3, 43.0, 24.8, 22.1, 18.0

Example 2

Preparation of 4-(3,5-dimethoxystyryl)phenyl-3-hydroxy-2-(hydroxymethyl)-2-methylpropanoate (compound 2-4)

Please refer to Scheme 2. To a stirred solution of compound 2-3 (0.900 g, 2.18 mmol) in CH$_2$Cl$_2$ (20 mL), 12 N HCl/MeOH (1:30, 2 ml) was added at room temperature. The reaction mixture was stirred at the same temperature for 30 minutes and then concentrated to give the crude product, which was then recrystallized to give compound 2-4 (0.66 g, 81% yield) as white solid.

$^1$H NMR (CDCl$_3$, 200 MHz): δ 7.50 (d, J=8.6 Hz, 2H), 7.19-6.99 (m, 4H), 6.64-6.63 (m, 2H), 6.38 (s, 1H), 4.05 (d, J=10.0 Hz, 2H), 3.85-3.80 (m, 8H), 2.89 (br s, 2H), 1.21 (s, 3H); $^{13}$C NMR (CDCl$_3$, 50 MHz): δ174.7, 160.9, 149.9, 139.1, 135.2, 129.0, 128.0, 127.5, 121.8, 104.5, 100.1, 68.7, 55.3, 49.5, 17.0. Melting point of compound 2-4:108.0-109.5° C.

For detailed synthesis of compound 3-3, 3-4, 3-5, and 3-6, please refer to Scheme 3.

Scheme 3

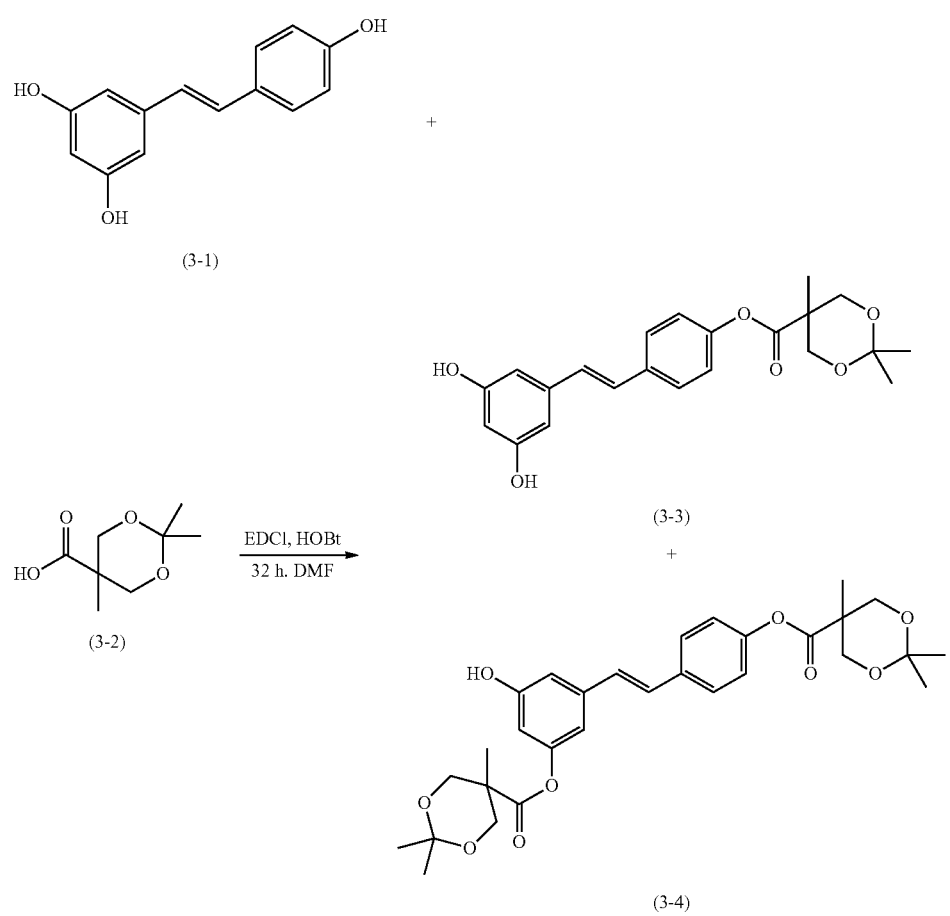

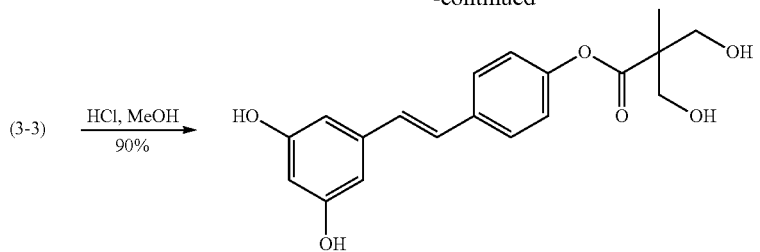

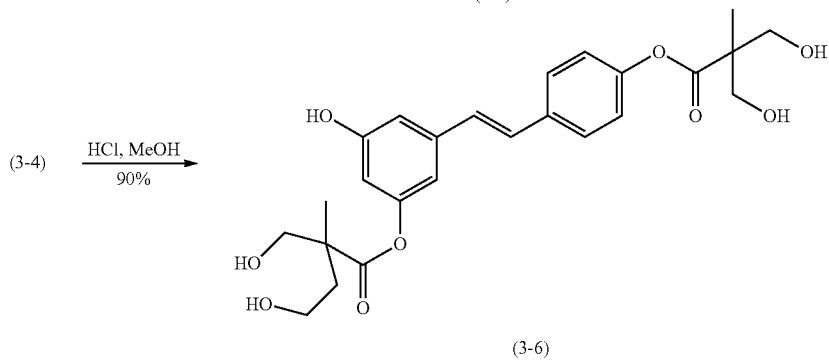

Example 3

Preparation of 4'-(2,2,5-trimethyl-1,3-dioxane-5-carboxy)-resveratrol (compound 3-3) and 3,4'-(2,2,5-trimethyl¬ 1,3-dioxane-5-carboxy)-resveratrol (compound 3-4)

To a stirred solution of compound 3-2 (1.373 g, 7.88 mmol) in DMF (25 mL), 1-ethyl-3-(3-dimethylaminopropyl)carbodiimide (EDCI, 1.224 g, 7.88 mmol), Hydroxybenzotriazole (HOBt, 1.065 g, 7.88 mmol), compound 3-1 (0.600 g, 2.62 mmol) and Et3N (0.797 g, 7.88 mmol) were added sequentially at room temperature. The reaction mixture was stirred at the same temperature for 32 hours and then H$_2$O (30 mL) was added. The combined organic extracts were washed with brine, dried over MgSO$_4$, filtered and concentrated to give the crude product, which was then purified by flash chromatography on silical gel with EtOAc/CH$_2$Cl$_2$/n-hexane (1:1:1) to afford compound 3-3 (0.537 g, 53% yield) as white solid and compound 3-4 (0.125 g, 9% yield) as white solid. Please note that compound 3-3 of this example is also the compound 1-3 of Scheme 1; compound 3-4 of this example is also the compound 1-4 in Scheme 1.

Compound 3-3: $^1$H NMR (CDCl$_3$, 500 MHz): δ 7.44 (d, J=6.5 Hz, 2H), 7.07 (d, J=6.5 Hz, 2H), 6.94-6.77 (m, 2H), 6.55 (s, 2H), 6.33 (s, 1H), 4.37 (d, J=12.0 Hz, 2H), 3.80 (d, J=12.0 Hz, 2H), 1.51 (s, 3H), 1.48 (s, 3H), 1.35 (s, 3H); $^{13}$C NMR (CDCl$_3$, 125 MHz): δ173.1, 157.5, 149.9, 139.5, 135.2, 128.7, 127.9, 127.4, 121.6, 121.7, 105.8, 102.6, 98.4, 66.0, 42.4, 25.3, 22.0, 18.4

Compound 3-4: $^1$H NMR (CDCl$_3$, 500 MHz): δ 7.49 (d, J=6.5 Hz, 2H), 7.11 (d, J=6.5 Hz, 2H), 7.09-6.91 (m, 2H), 6.84 (s, 2H), 6.53 (s, 1H), 4.36 (d, J=11.0 Hz, 4H), 3.80 (d, J=11.5 Hz, 4H), 1.51 (s, 6H), 1.48 (s, 6H), 1.38 (s, 6H); $^{13}$C NMR (CDCl$_3$, 125 MHz): δ173.2, 157.3, 151.9, 150.5, 139.6, 134.8, 129.0, 127.7, 127.6, 121.7, 111.7, 111.1, 108.3, 98.3, 66.0, 42.3, 25.1, 22.2, 18.5

Example 4

Preparation of 4'-[2,2-Bis(hydroxymethyl)propanoxy]-resveratrol (compound 3-5)

To a stirred solution of compound 3-3 (0.232 g, 0.60 mmol) in CH$_2$Cl$_2$ (10 mL), 12 N HCl/MeOH (1:30, 1 mL) was added at room temperature. The reaction mixture was stirred at the same temperature for 30 minutes and then concentrated to give the crude product, which was then recrystallized to give compound 3-5 (0.188 g, 90% yield) as white solid. Please note that compound 3-5 of this example is also the compound 1-8 of Scheme 1.

$^1$H NMR (MeOD, 200 MHz): δ 7.65 (d, J=8.6 Hz, 2H), 7.23-7.07 (m, 4H), 6.64-6.63 (m, 2H), 6.35 (s, 1H), 3.98 (d, J=10.0 Hz, 2H), 3.87 (d, J=10.0 Hz, 2H), 1.43 (s, 3H); $^{13}$C NMR (MeOD, 50 MHz): δ172.5, 156.8, 148.8, 137.7, 133.6, 127.3, 125.5, 125.4, 120.2, 103.2, 100.3, 63.0, 49.2, 14.4. Melting point of compound 3-5: 138.0-139.5° C.

Example 5

Preparation of 3,4'-[2,2-Bis(hydroxymethyl)propanoxy]-resveratrol (compound 3-6)

To a stirred solution of compound 3-4 (0.098 g, 0.18 mmol) in CH$_2$Cl$_2$ (2 mL), 12 N HCl/MeOH (1:30, 0.2 mL) was added at room temperature. The reaction mixture was stirred at the same temperature for 30 minutes and then concentrated to give the crude product, which was then recrystallized to give compound 3-6 (0.075 g, 90% yield) as white solid. Please note that compound 3-6 of this example is also the compound of 1-9 in Scheme 1.

$^1$H NMR (MeOD, 500 MHz): δ 7.58 (d, J=8.0 Hz, 2H), 7.20-7.05 (m, 4H), 6.87-6.84 (m, 2H), 6.49 (s, 1H), 3.87 (d, J=11.0 Hz, 4H), 3.77 (d, J=11.0 Hz, 4H), 1.32 (s, 6H); $^{13}$C NMR (MeOD, 125 MHz): δ172.5, 158.2, 152.2, 150.6, 139.4, 134.9, 128.2, 127.1, 121.7, 110.5, 108.0, 64.5, 50.8, 50.7, 50.6, 16.0, 15.9. Melting point of compound 3-6: 146.0-148.0° C.

Example 6

Preparation of 3,5,4'-[2,2-Bis(hydroxymethyl)propanoxy]-resveratrol (compound 4-3)

For preparation of compound 4-3, please refer to Scheme 4.

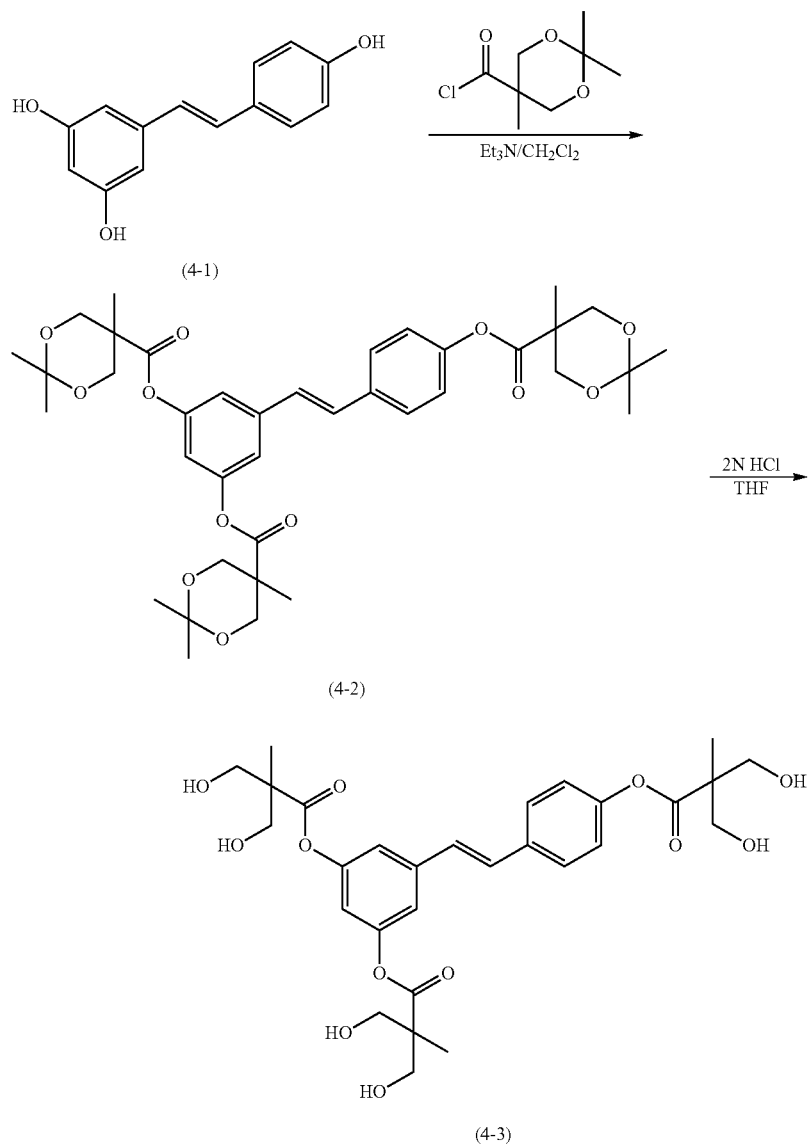

To a solution of compound 4-1 (228 mg, 1.0 mmol) in methylene chloride (5.0 mL), 2,2,5-trimethyl-1,3-dioxane-5-carbonyl chloride (636 mg, 3.3 mmol) and triethylamine (0.55 mL, 3.96 mmol) were slowly added and then stirred at room temperature for 1.0 hour. The reaction mixture was quenched with water and extracted with methylene chloride. The organic layer was washed with brine, dried over MgSO$_4$(s), and concentrated under reduced pressure. The residue was then purified by column chromatography on silica gel to provide compound 4-2.

To a solution of compound 4-2 (348 mg, 0.5 mmol) in THF (3.0 mL), 2N HCl(aq) (3.0 mL) was slowly added and then stirred at room temperature for 1.0 hour. The solution was diluted with water and extracted with EtOAc. The organic layer was washed with brine, dried over MgSO$_4$(s), and concentrated under reduced pressure. The residue was then purified by column chromatography on silica gel to provide compound 4-3 (230 mg, 0.4 mmol) in 80% yield. Please note that compound 4-2 of this example is also the compound 1-5 in Scheme; compound 4-3 of this example is also the compound 1-10 of Scheme 1.

$^1$H NMR (500 MHz, DMSO-d$^6$): δ: 1.21 (s, 9H), 3.52-3.55 (m, 6H), 3.65-3.70 (m, 6H), 4.90-4.96 (m, 6H), 6.78 (s, 1H), 7.09 (d, 2H), 7.22 (d, 2H), 7.27 (d, 2H), 7.66 (d, 2H). MS: 577 (M+1). Melting point of compound 4-3: 228.0-229.5° C.

Example 7

Preparation of 5-[2,2-Bis(hydroxymethyl)propanoxy]-resveratrol (compound 5-3)

For the preparation of compound 5-3, please refer to Scheme 5.

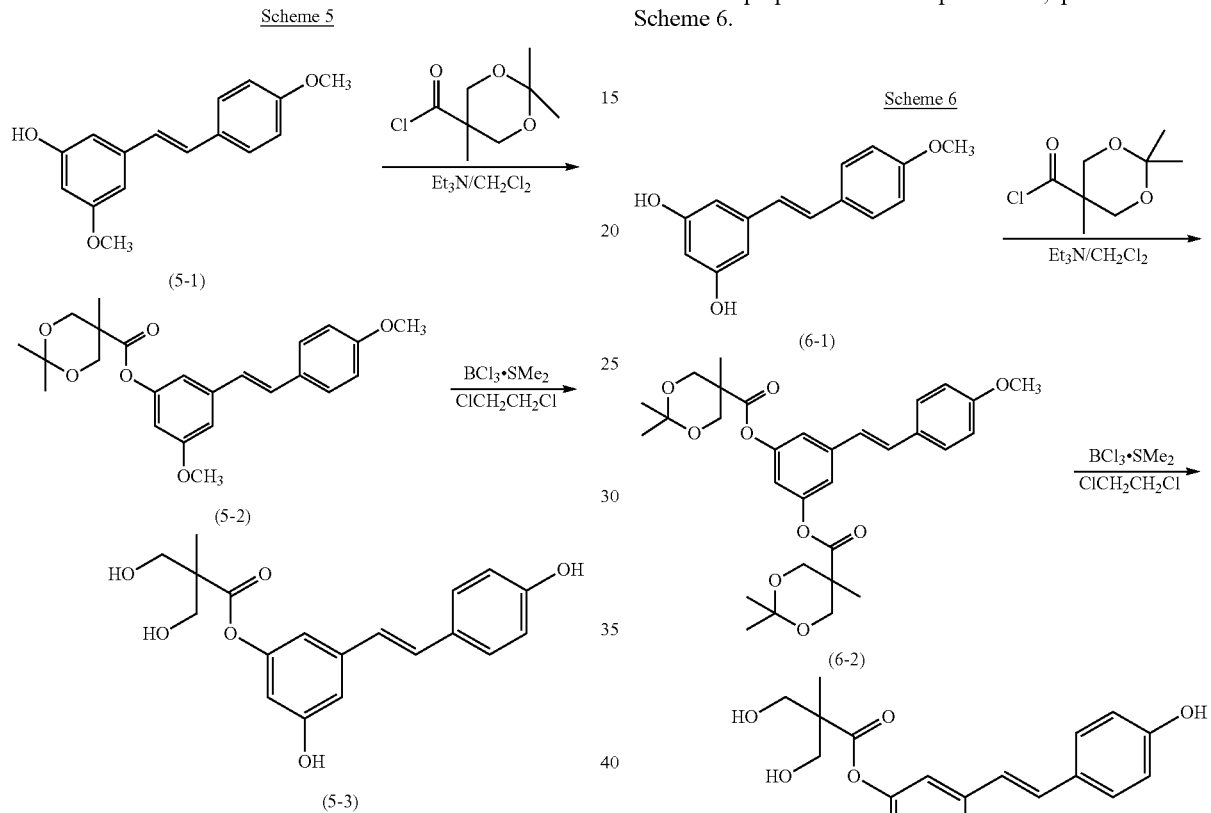

To a solution of compound 5-1 (256 mg, 1.0 mmol) in methylene chloride (5.0 mL), 2,2,5-trimethyl-1,3-dioxane-5-carbonyl chloride (212 mg, 1.1 mmol) and triethylamine (0.17 mL, 1.2 mmol) were slowly added and then stirred at room temperature for 1.0 hour. The reaction mixture was quenched with water and extracted with methylene chloride. The organic layer was washed with brine, dried over $MgSO_4(s)$, and concentrated under reduced pressure. The residue was then purified by column chromatography on silica gel to provide compound 5-2.

To a solution of compound 5-2 (412 mg, 1.0 mmol) in 1,2-dichloroethane (10 mL), $BCl_3 \cdot SMe_2$ (2.0M in $CH_2Cl_2$, 2.5 mL, 5.0 mmol) was slowly added and then heated to reflux for 16 hours. The reaction mixture was cooled to room temperature, quenched with water and extracted with EtOAc. The organic layer was washed with brine, dried over $MgSO_4(s)$, and concentrated under reduced pressure. The residue was then purified by column chromatography on silica gel to provide compound 5-3 (207 mg, 0.6 mmol) in 60% yield. Please note that the compound 5-3 of this example is also the compound 1-11 of Scheme 1.

$^1$H NMR (500 MHz, DMSO-d$^6$): δ: 1.19 (s, 3H), 3.52 (d, 4H), 3.65 (d, 3H), 4.90 (s, 2H), 6.35 (t, 1H), 6.70 (s, 1H), 6.74-6.78 (m, 3H), 6.90 (d, 1H), 7.02 (d, 1H), 7.41 (d, 2H), 9.64 (s (br.), 2H). MS: 345 (M+1). Melting point of compound 5-3:135.6-136.9° C.

Example 8

Preparation of 3,5-[2,2-Bis(hydroxymethyl)propanoxy]-resveratrol (compound 6-3)

For the preparation of compound 6-3, please refer to Scheme 6.

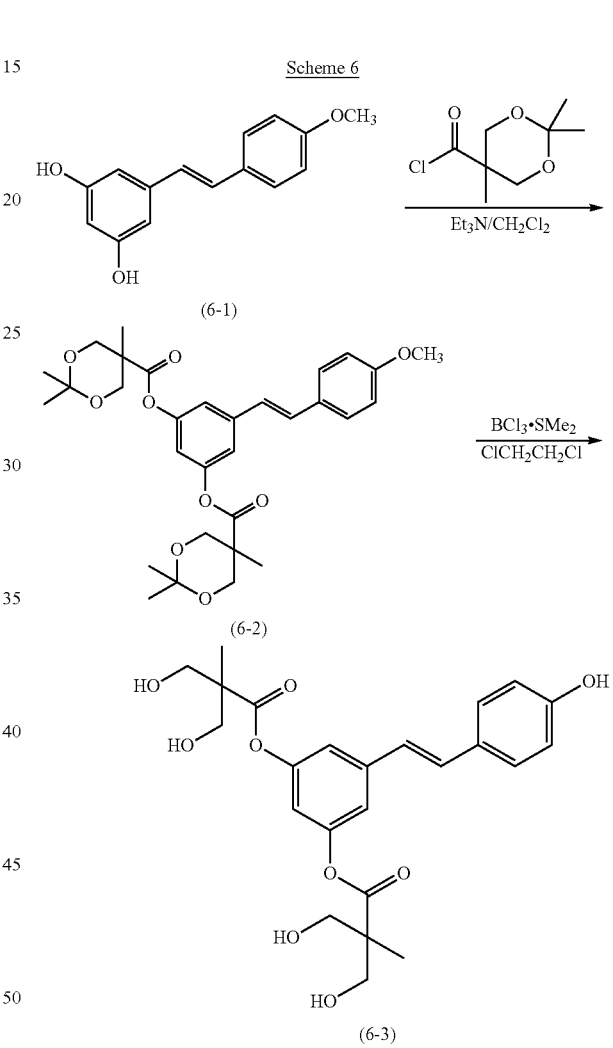

To a solution of compound 6-1 (242 mg, 1.0 mmol) in methylene chloride (5.0 mL), 2,2,5-trimethyl-1,3-dioxane-5-carbonyl chloride (424 mg, 2.2 mmol) and triethylamine (0.37 mL, 2.64 mmol) were slowly added and then stirred at room temperature for 1.0 hour. The reaction mixture was quenched with water and extracted with methylene chloride. The organic layer was washed with brine, dried over $MgSO_4(s)$, and concentrated under reduced pressure. The residue was then purified by column chromatography on silica gel to provide compound 6-2.

To a solution of compound 6-2 (554 mg, 1.0 mmol) in 1,2-dichloroethane (10 mL), $BCl_3 \cdot SMe_2$ (2.0M in $CH_2Cl_2$, 2.5 mL, 5 mmol) was slowly added and then heated to reflux for 16 hours. The reaction mixture was cooled to room temperature, quenched with water and extracted with EtOAc. The organic layer was washed with brine, dried over MgSO$_4$(s), and concentrated under reduced pressure. The residue was then purified by column chromatography on silica gel to provide compound 6-3 (300 mg, 0.65 mmol) in 65% yield. Please note that the compound 6-3 of this example is also the compound 1-12 of Scheme 1.

$^1$H NMR (500 MHz, DMSO-d$^6$): δ: 1.20 (s, 6H), 3.53 (m, 4H), 3.68 (m, 4H), 4.95 (m, 3H), 6.71 (m, 1H), 6.77 (d, 2H), 7.00-7.03 (m, 1H), 7.15 (m, 3H), 7.45 (d, 2H). MS: 461 (M+1). Melting point of compound 6-3:195.0-197.0° C.

Example 9

Preparation of 3,4'methyl-5-[2,2-Bis(hydroxymethyl)propanoxy]-resveratrol (compound 7-3)

For the preparation of compound 7-3, please refer to Scheme 7.

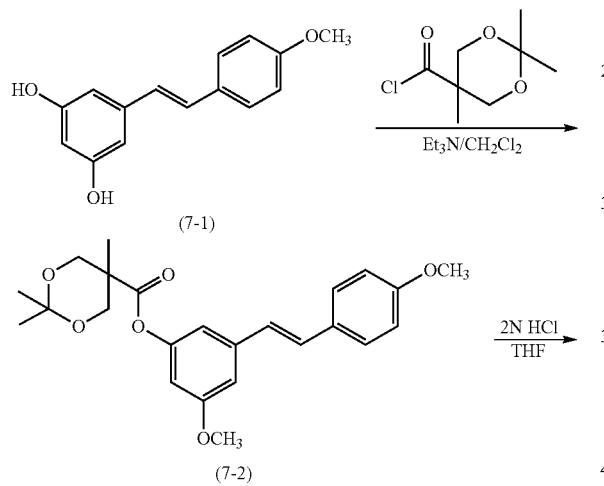

To a solution of compound 7-1 (256 mg, 1.0 mmol) in methylene chloride (5.0 mL), 2,2,5-trimethyl-1,3-dioxane-5-carbonyl chloride (212 mg, 1.1 mmol) and triethylamine (0.17 mL, 1.2 mmol) were slowly added and then stirred at room temperature for 1.0 hour. The reaction mixture was quenched with water and extracted with methylene chloride. The organic layer was washed with brine, dried over MgSO$_4$(s), and concentrated under reduced pressure. The residue was then purified by column chromatography on silica gel to provide compound 7-2.

To a solution of compound 7-2 (206 mg, 0.5 mmol) in THF (3.0 mL), 2N HCl(aq) (3.0 mL) was slowly added and then stirred at room temperature for 1.0 hour. The solution was diluted with water and extracted with EtOAc. The organic layer was washed with brine, dried over MgSO$_4$(s), and concentrated under reduced pressure. The residue was then purified by column chromatography on silica gel to provide compound 7-3 (158 mg, 0.42 mmol) in 84% yield.

$^1$H NMR (500 MHz, DMSO-d$^6$): δ: 1.20 (s, 3H), 3.54 (m, 2H), 3.68 (m, 2H), 3.78 (s, 6H), 4.89 (s, 2H), 6.53 (s, 1H), 6.87 (s, 1H), 6.94 (d, 2H), 7.04 (t, 2H), 7.19 (d, 1H), 7.54 (d, 2H). MS: 372.9 (M+1). Melting point of compound 7-3:101.0-102.5° C.

Example 10

Preparation of 3-methyl-5,4'-[2,2-Bis(hydroxymethyl)propanoxy]-resveratrol (compound 8-3)

For the preparation of compound 8-3, please refer to Scheme 8.

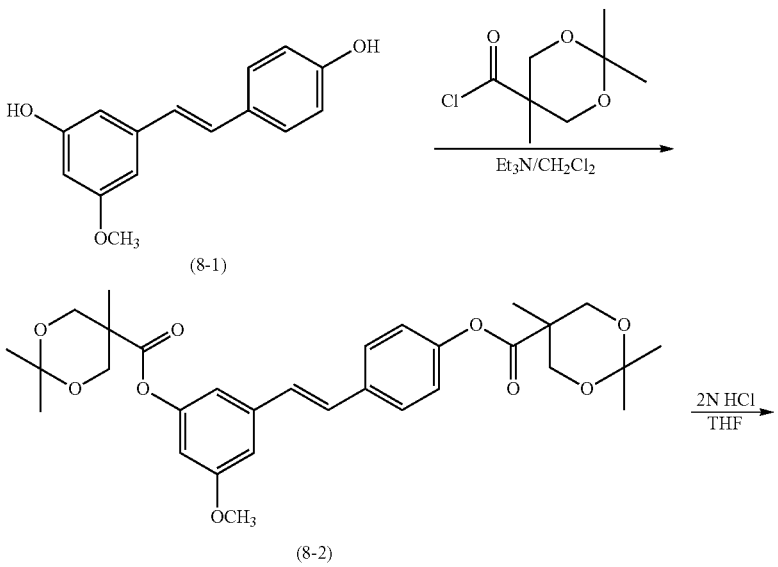

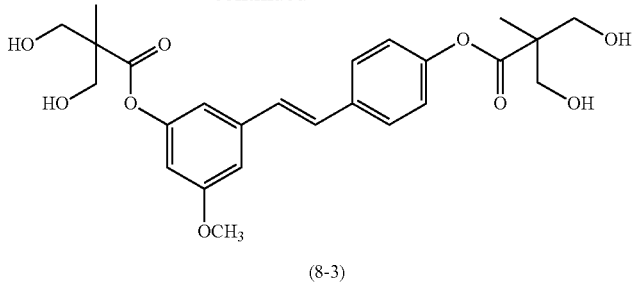

(8-3)

To a solution of compound 8-1 (242 mg, 1.0 mmol) in methylene chloride (5.0 mL), 2,2,5-trimethyl-1,3-dioxane-5-carbonyl chloride (424 mg, 2.2 mmol) and triethylamine (0.42 mL, 3.0 mmol) were slowly added and then stirred at room temperature for 1.0 hour. The reaction mixture was quenched with water and extracted with methylene chloride. The organic layer was washed with brine, dried over $MgSO_4(s)$, and concentrated under reduced pressure. The residue was then purified by column chromatography on silica gel to provide compound 8-2.

To a solution of compound 8-2 (277 mg, 0.5 mmol) in THF (3.0 mL), 2N HCl(aq) (3.0 mL) was slowly added and then stirred at room temperature for 1.0 hour. The solution was diluted with water and extracted with EtOAc. The organic layer was washed with brine, dried over $MgSO_4(s)$, and concentrated under reduced pressure. The residue was then purified by column chromatography on silica gel to provide compound 8-3 (190 mg, 0.4 mmol) in 80% yield.

$^1$H NMR (500 MHz, DMSO-d$^6$): δ: 1.20 (s, 6H), 3.53 (m, 4H), 3.67 (m, 4H), 3.79 (s, 3H), 4.93 (t, 4H), 6.57 (t, 1H), 6.92 (s, 1H), 7.06-7.09 (m, 3H), 7.18-7.29 (m, 2H), 7.63 (d, 2H). MS: 475.4 (M+1). Melting point of compound 8-3:168.0-169.5° C.

Example 11

Preparation of 3,5-acetyl-4'-[2,2-Bis(hydroxymethyl)propanoxy]-resveratrol (compound 9-4)

For the preparation of compound 9-4, please refer to Scheme 9.

Scheme 9

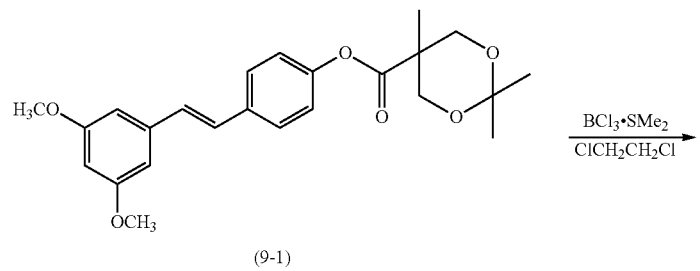

(9-1)

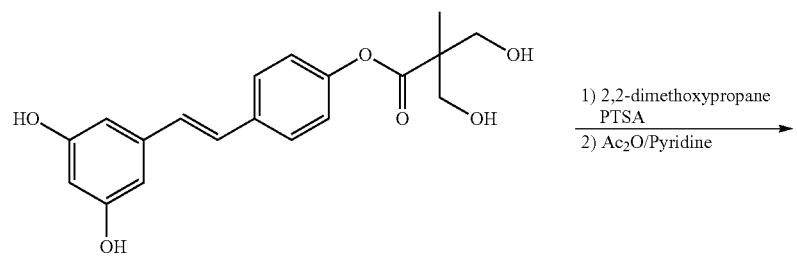

(9-2)

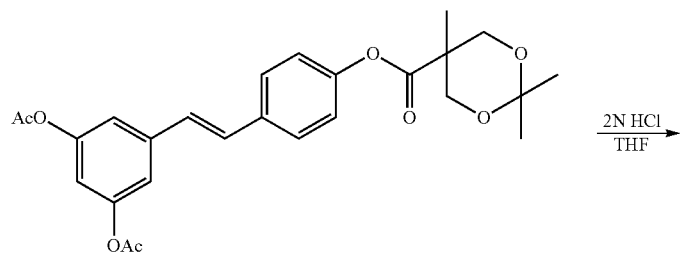

(9-3)

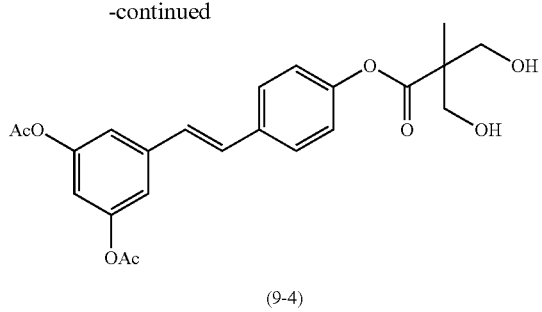

(9-4)

To a solution of compound 9-1 (824 mg, 2.0 mmol) in 1,2-dichloroethane (20 mL), BCl$_3$.SMe$_2$ (2.0M in CH$_2$Cl$_2$, 5.0 mL, 10 mmol) was slowly added and then heated to reflux for 16 hours. The reaction mixture was cooled to room temperature, quenched with water and extracted with EtOAc. The organic layer was washed with brine, dried over MgSO$_4$(s), and concentrated under reduced pressure. The residue was then purified by column chromatography on silica gel to provide compound 9-2.

A solution of compound 9-2 (230 mg, 0.67 mmol) and catalytic amount of PTSA in 2,2-dimethoxypropane (5.0 mL) was stirred at room temperature for 1.0 hour. The reaction mixture was then added with NaHCO$_3$ and further stirred for 15 minutes. The solution was concentrated under reduced pressure to remove 2,2-dimethoxypropane, and then quenched with water and extracted with methylene chloride. The organic layer was washed with brine, dried over MgSO$_4$(s), and concentrated under reduced pressure. The residue was dissolved in pyridine (2.0 mL), added with acetic anhydride (2.0 mL) and stirred at room temperature for 2.0 hours. The reaction mixture was quenched with water and extracted with EtOAc. The organic layer was washed with brine, dried over MgSO$_4$(s), and concentrated under reduced pressure. The residue was then purified by column chromatography on silica gel to provide compound 9-3.

To a solution of compound 9-3 in THF (3.0 mL), 2N HCl(aq) (3.0 mL) was slowly added and then stirred at room temperature for 1.0 hour. The solution was diluted with water and extracted with EtOAc. The organic layer was washed with brine, dried over MgSO$_4$(s), and concentrated under reduced pressure. The residue was purified by column chromatography on silica gel to provide compound 9-4 (172 mg, 0.4 mmol) in 60% yield.

$^1$H NMR (500 MHz, DMSO-d$^6$): δ: 1.20 (s, 3H), 2.29 (s, 3H), 3.53 (m, 2H), 3.68 (m, 2H), 4.93 (t, 2H), 6.90 (t, 1H), 7.10 (d, 2H), 7.21 (d, 1H), 7.30 (m, 3H), 7.63 (d, 2H). MS: 429.1 (M+1). Melting point of compound 9-4:121.0-122.5° C.

Example 12

Preparation of 3-acetyl-5,4'-[2,2-Bis(hydroxymethyl) propanoxy]-resveratrol (compound 10-4)

For the preparation of compound 1004, please refer to Scheme 10.

Scheme 10

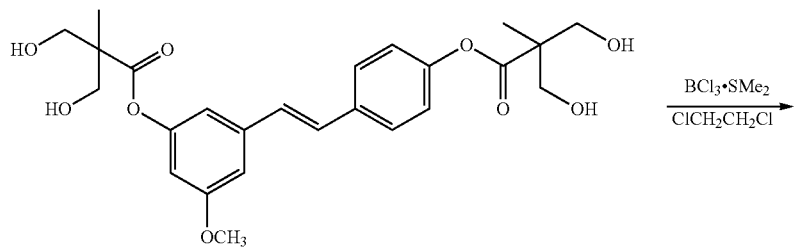

(10-1)

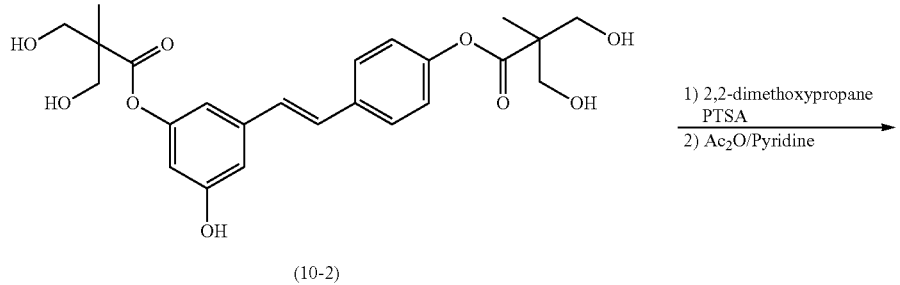

(10-2)

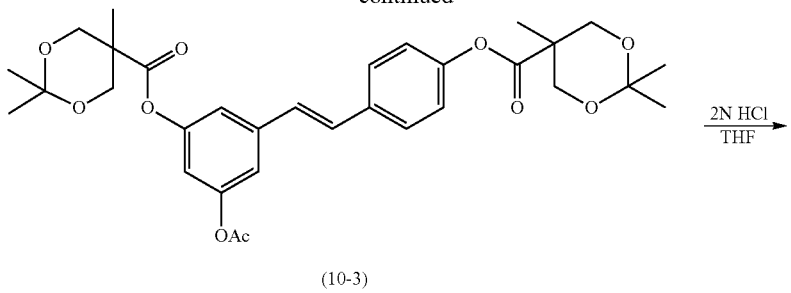

(10-3)

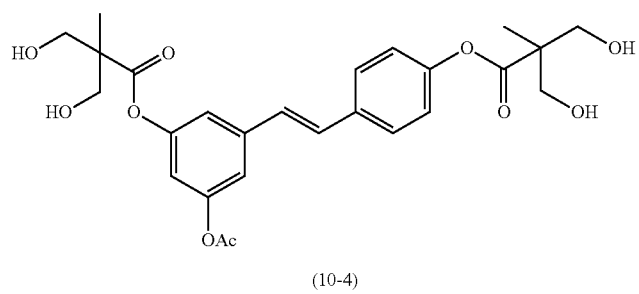

(10-4)

To a solution of compound 10-1 (456 mg, 0.96 mmol) in 1,2-dichloroethane (10 mL), BCl$_3$.SMe$_2$ (2.0M in CH$_2$Cl$_2$, 2.5 mL, 5.0 mmol) was slowly added and then heated to reflux for 16 hours. The reaction mixture was cooled to room temperature, quenched with water and extracted with EtOAc. The organic layer was washed with brine, dried over MgSO$_4$(s), and concentrated under reduced pressure. The residue was purified by column chromatography on silica gel to provide compound 10-2.

A solution of compound 10-2 and catalytic amount of PTSA in 2,2-dimethoxypropane (5.0 mL) was stirred at room temperature for 1.0 hour. The reaction mixture was then added with NaHCO$_3$ and further stirred for 15 minutes. The solution was concentrated under reduced pressure to remove 2,2-dimethoxypropane, and then quenched with water and extracted with methylene chloride. The organic layer was washed with brine, dried over MgSO$_4$(s), and concentrated under reduced pressure. The residue was dissolved in pyridine (2.0 mL), added with acetic anhydride (2.0 mL) and stirred at room temperature for 2.0 hours. The reaction mixture was quenched with water and extracted with EtOAc. The organic layer was washed with brine, dried over MgSO$_4$(s), and concentrated under reduced pressure. The residue was purified by column chromatography on silica gel to provide compound 10-3.

To a solution of compound 10-3 (291 mg, 0.5 mmol) in THF (3.0 mL), 2N HCl(aq) (3.0 mL) was slowly added and then stirred at room temperature for 1.0 hour. The solution was diluted with water and extracted with EtOAc. The organic layer was washed with brine, dried over MgSO$_4$(s), and concentrated under reduced pressure. The residue was then purified by column chromatography on silica gel to provide compound 10-4 (216 mg, 0.43 mmol) in 85% yield. Please note that compound 10-1 of Scheme 10 is also compound 8-3 of Scheme 8.

$^1$H NMR (500 MHz, DMSO-d$^6$): δ: 1.19 (s, 3H), 1.21 (s, 6H), 2.27 (s, 3H), 3.51 (m, 4H), 3.66 (m, 4H), 4.93 (m, 4H), 6.82 (t, 1H), 7.07 (d, 2H), 7.21-7.32 (m, 4H), 7.63 (d, 2H). MS: 503.5 (M+1)° Melting point of compound 10-4: 161.0-163.0° C.

Example 13

Preparation of 3-methyl-4'-[2,2-Bis(hydroxymethyl) propanoxy]-resveratrol (compound 11-3)

For the preparation of compound 11-3, please refer to Scheme 11.

Scheme 11

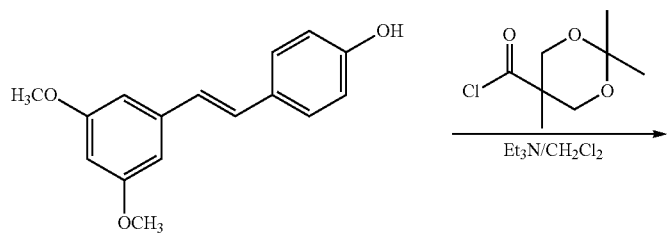

(11-1)

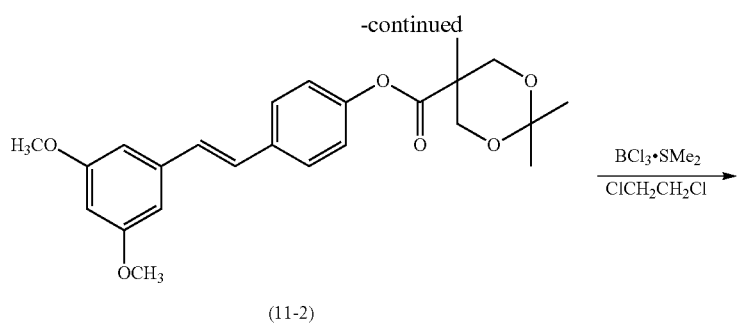

(11-2)

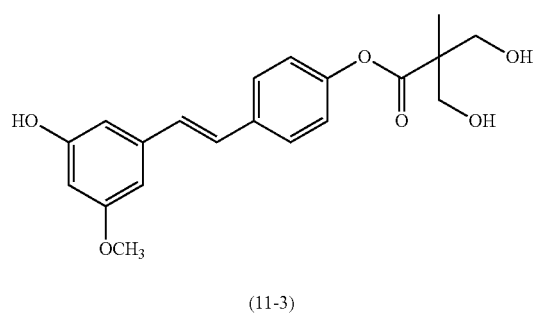

(11-3)

To a solution of compound 11-1 (1.1 g, 4.3 mmol) in methylene chloride (10 mL), 2,2,5-trimethyl-1,3-dioxane-5-carbonyl chloride (913 mg, 4.7 mmol) and triethylamine (0.9 mL, 6.5 mmol) were slowly added and then stirred at room temperature for 1.0 hour. The reaction mixture was quenched with water and extracted with methylene chloride. The organic layer was washed with brine, dried over $MgSO_4(s)$, and concentrated under reduced pressure. The residue was purified by column chromatography on silica gel to provide compound 11-2.

To a solution of compound 11-2 (824 mg, 2.0 mmol) in 1,2-dichloroethane (20 mL), $BCl_3.SMe_2$ (2.0M in $CH_2Cl_2$, 5.0 mL, 10 mmol) was slowly added and then heated to reflux for 5.0 hours. The reaction mixture was cooled to room temperature, quenched with water and extracted with EtOAc. The organic layer was washed with brine, dried over $MgSO_4(s)$, and concentrated under reduced pressure. The residue was then purified by column chromatography on silica gel to provide compound 11-3 (287 mg, 0.8 mmol) in 40% yield.

$^1$H NMR (500 MHz, DMSO-d$^6$): δ: 1.20 (s, 6H), 3.52 (m, 2H), 3.67 (m, 2H), 3.73 (s, 3H), 4.92 (t, 2H), 6.26 (s, 1H), 6.57-6.63 (d, 2H), 7.06-7.17 (m, 4H), 7.61 (d, 2H), 9.47 (s, 1H). MS: 359.2 (M+1). Melting point of compound 11-3: 129.0-131.0° C.

Example 14

Preparation of 5-acetyl-3-methyl-4'-[2,2-Bis(hydroxymethyl)propanoxy]-resveratrol (compound 12-3)

For the preparation of compound 12-3, please refer to Scheme 12.

Scheme 12

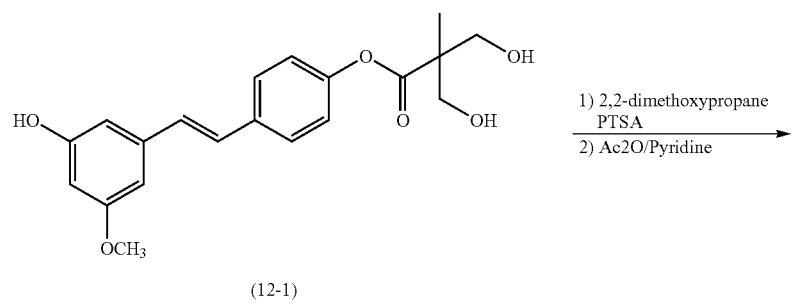

(12-1)

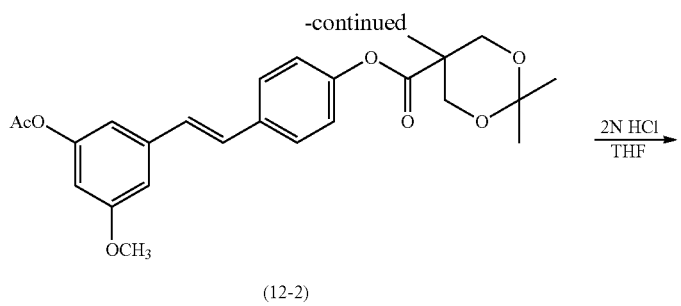

(12-2)

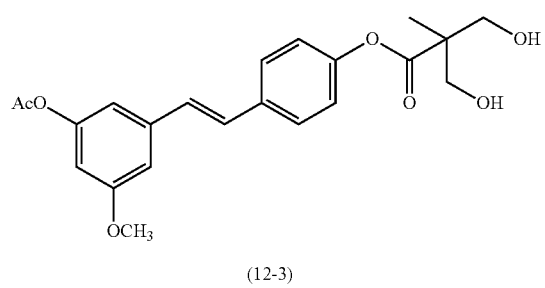

(12-3)

A solution of compound 12-1 (716 mg, 2 mmol) and catalytic amount of PTSA in 2,2-dimethoxypropane (10 mL) was stirred at room temperature for 1.0 hour. The reaction mixture was then added with NaHCO$_3$ and further stirred for 15 minutes. The solution was concentrated under reduced pressure to remove 2,2-dimethoxypropane, and then quenched with water and extracted with methylene chloride. The organic layer was washed with brine, dried over MgSO$_4$(s), and concentrated under reduced pressure. The residue was dissolved in pyridine (4.0 mL), added with acetic anhydride (4.0 mL) and stirred at room temperature for 2.0 hours. The reaction mixture was quenched with water and extracted with EtOAc. The organic layer was washed with brine, dried over MgSO$_4$(s), and concentrated under reduced pressure. The residue was purified by column chromatography on silica gel to provide compound 12-2.

To a solution of compound 12-2 in THF (10 mL), 2N HCl(aq) (10 mL) was slowly added and then stirred at room temperature for 1.0 hour. The solution was diluted with water and extracted with EtOAc. The organic layer was washed with brine, dried over MgSO$_4$(s), and concentrated under reduced pressure. The residue was purified by column chromatography on silica gel to provide compound 12-3 (560 mg, 1.4 mmol) in 70% yield. Please note that compound 12-1 of Scheme 12 is also compound 11-3 of Scheme 11.

$^1$H NMR (500 MHz, DMSO-d$^6$): δ: 1.20 (s, 3H), 2.27 (s, 3H), 3.53 (m, 2H), 3.67 (m, 2H), 3.79 (s, 3H), 4.93 (t, 2H), 6.64 (s, 1H), 6.98 (s, 1H), 7.08 (t, 3H), 7.18 (d, 1H), 7.30 (d, 1H), 7.63 (d, 2H). MS: 401.1 (M+1). Melting point of compound 12-3:109.0-111.0° C.

Example 15

Preparation of 3,5-[2,2-Bis(hydroxymethyl)propanoxy]-4'-methyl-resveratrol (compound 13-3)

For the preparation of compound 13-3, please refer to Scheme 13.

Scheme 13

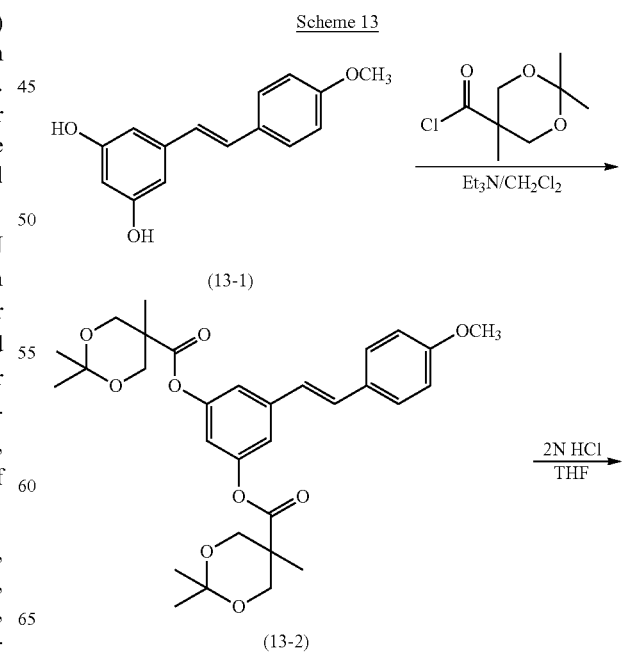

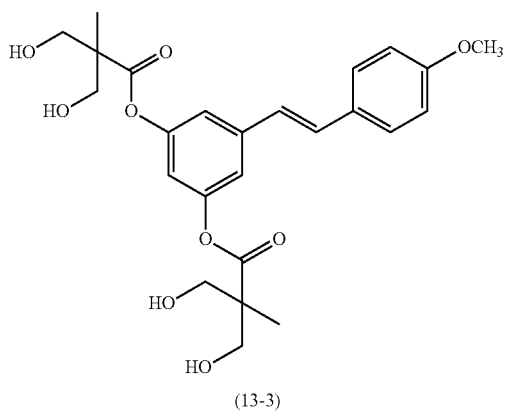

(13-3)

To a solution of compound 13-1 (242 mg, 1.0 mmol) in methylene chloride (5.0 mL), 2,2,5-trimethyl-1,3-dioxane-5-carbonyl chloride (424 mg, 2.2 mmol) and triethylamine (0.37 mL, 2.64 mmol) was slowly added and then stirred at room temperature for 1.0 hour. The reaction mixture was quenched with water and extracted with methylene chloride. The organic layer was washed with brine, dried over $MgSO_4(s)$, and concentrated under reduced pressure. The residue was purified by column chromatography on silica gel to provide compound 13-2.

To a solution of compound 13-2 (277 mg, 0.5 mmol) in THF (3.0 mL) was slowly added 2N HCl(aq) (3.0 mL) and then stirred at room temperature for 1.0 hour. The solution was diluted with water and extracted with EtOAc. The organic layer was washed with brine, dried over $MgSO_4(s)$, and concentrated under reduced pressure. The residue was then purified by column chromatography on silica gel to provide compound 13-3 (197 mg, 0.42 mmol) in 84% yield.

$^1$H NMR (500 MHz, DMSO-d$^6$): δ: 1.21 (s, 6H), 3.53 (m, 4H), 3.68 (m, 4H), 3.77 (m, 4H), 4.93 (m, 4H), 6.73 (t, 1H), 6.95 (d, 2H), 7.17 (m, 4H), 7.55 (d, 2H). MS: 475 (M+1). Melting point of compound 13-3:141.0-142.5° C.

Example 16

Preparation of Pterostilbene D-Ribonic Acid Diacetonide (Compound 14-5)

For preparation of compound 14-5, please refer to Scheme 14.

Scheme 14

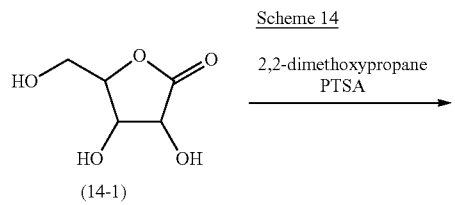

(14-1)

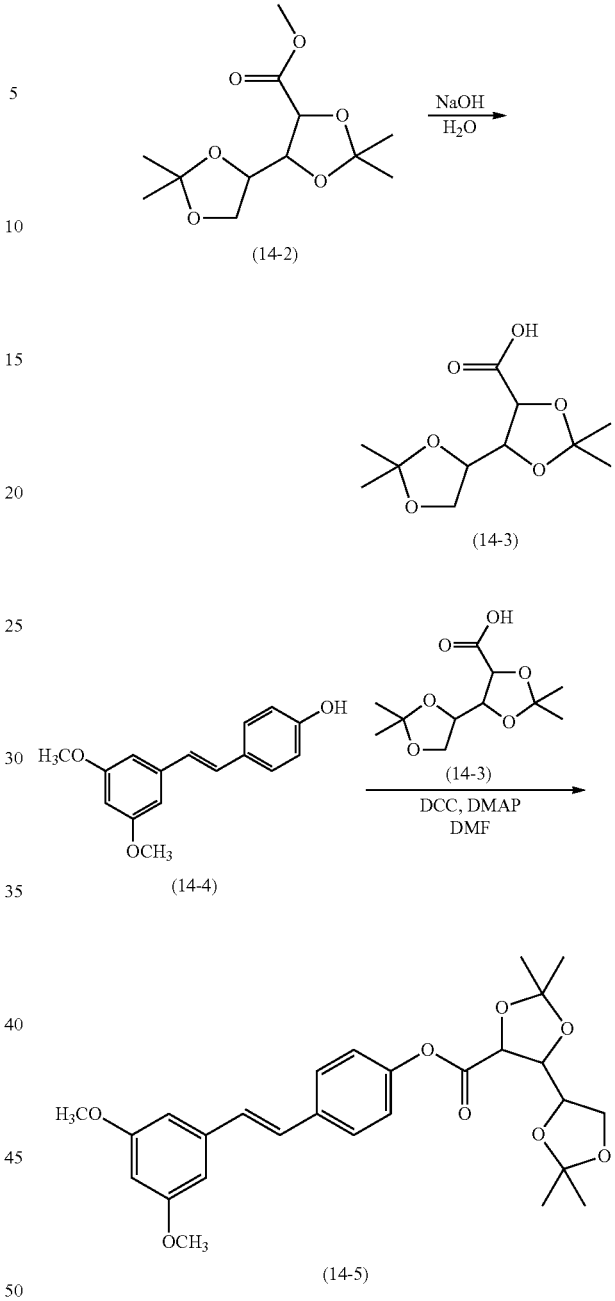

A solution of compound 14-1 (1.484 g, 10 mmol) and PTSA (114 mg, 0.6 mmol) in 2,2-dimethoxypropane (20 mL) was stirred at room temperature for 48 hours. The reaction mixture was then added with $NaHCO_3$ and further stirred for 15 minutes. The solution was concentrated under reduced pressure to remove 2,2-dimethoxypropane, and then quenched with water and extracted with methylene chloride. The organic layer was washed with brine, dried over $MgSO_4(s)$, and concentrated under reduced pressure to provide compound 14-2.

A solution of compound 14-2 (5.047 g, 19.4 mmol) in water (20 mL) was cooled to 0° C. and stirred for 20 minutes. The solution was then warmed to room temperature and stirred for further 70 minutes. The reaction mixture was added with water and extracted with methylene chloride. The aqueous layer was acidified by adding citric acid (15.42 g, 73.4 mmol) at 0° C., and extracted with methylene chloride for 4 times. The aqueous layer was then added with NaCl (5.0 g) and extracted with methylene chloride for further 3 times. Combined the organic layer, dried over $MgSO_4(s)$, and concentrated under reduced pressure to provide compound 14-3.

To a solution of compound 14-4 (2.2 g, 8.6 mmol) in DMF, compound 14-3 (3.19 g. 13.0 mmol), dicyclohexylcarbodiimide (2.96 g, 14.3 mmol) and 4-dimethylaminopyridine (71.4 mg, 0.6 mmol) were added stepwisely and then stirred at room temperature for 18 hours. The reaction mixture was quenched with water and extracted with methylene chloride. The organic layer was washed with brine, dried over $MgSO_4(s)$, and concentrated under reduced pressure. The residue was purified by column chromatography on silica gel to provide compound 14-5 (3.0 g, 6.2 mmol) in 72% yield.

$^1$H NMR (500 MHz, DMSO-d$^6$): δ: 1.29 (s, 3H), 1.35 (s, 3H), 1.36 (s, 3H), 1.47 (s, 3H), 3.78 (s, 6H), 3.86 (m, 1H), 4.12 (m, 2H), 4.39 (m, 1H), 5.04 (d, 1H), 6.42 (t, 1H), 6.78 (d, 2H), 7.19 (m, 3H), 7.27 (d, 1H), 7.66 (d, 2H). MS: 485.0 (M+1). Melting point of compound 14-5:107.0-109.0° C.

The acetonide protection group of compound 14-5 could be deprotected by using one of many available acetonide deprotection methods known to the art to give Pterostilbene D-ribonic acid (compound of 14-6).

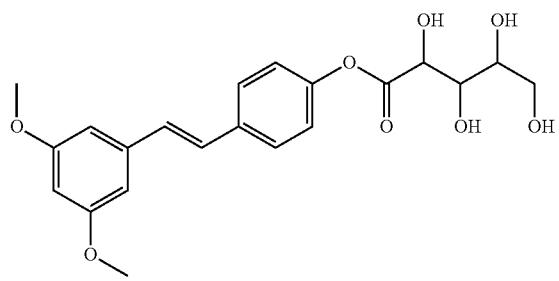 [SMILES: COc1cc(/C=C/c2ccc(OC(=O)C(O)C(O)C(O)CO)cc2)cc(OC)c1]

Cell Lines and Culture

The human head and neck carcinoma cell line CAL27 was obtained from American Tissue Culture Collection (ATCC). The cisplatin-resistant cell line CAR (CAL27-cisplatin resistance) was established by clonal selection of CAL27 using 10 cycles of 1 passage treatment with 10-80 μM of cisplatin (Sigma-Aldrich Corp. (St. Louis, Mo., USA) followed by a recovery period of another passage. CAR cells were cultivated in Dulbecco's modified Eagle's medium (DMEM) supplemented with 10% FBS, 100 μg/mL streptomycin, 100 U/mL penicillin G, 2 mM L-glutamine (Gibco by Life Technologies (Carlsbad, Calif., USA)) and 80 μM of cisplatin (Sigma-Aldrich Corp. (St. Louis, Mo., USA).

MTT Assay

Antiproliferations of compound 2-4 were determined by an improved MTT assay. The CAR cells were individually plated at a density of $2\times10^4$ cells/well onto 96-well plates and treated with Dimethyl sulfoxide (DMSO) alone (0.5% (v/v) in media served as a vehicle control) and various concentrations (0, 25, 50, 75 and 100 μM) of compound 2-4 for 24 and 48 hours. Following the above treatments, the supernatant was discarded before a 100 μL solution of MTT (500 μg/ml) was added to each well for 4 hours at 37□. After incubation, the medium was replaced by the addition of 200 μL DMSO to solubilize the violet formazan crystal produced from MTT. The absorbance of the dissolved formazan grained within the cells was measured at 570 nm by a microplate reader to calculate viability (data shown as % of control).

Animal Administration

All animal experiments of the invention complied with institutional guidelines (Affidavit of Approval of Animal Use Protocol) approved by the Institutional Animal Care and Use Committee (IACUC) of China Medical University (Taichung, Taiwan). All pathogen-free four-week-old male BALB/c nude mice were purchased from the National Laboratory Animal Center (Taipei, Taiwan). These animals were housed at a constant room temperature with a regular 12-hour light/12-hour dark cycle and hereafter fed a standard rodent diet and water ad libitum.

Xenograft Antitumor Study

The CAR cells ($1\times10^7$ cells/mouse) in 0.2 mL (1:1) cultural medium and Matrigel (BD Biosciences) were subcutaneously injected into the flank of nude mice. When xenograft tumors reached approximately 50 mm$^3$ (at day 22 after cell inoculation), thirty two mice were randomly divided into four groups with eight mice in each group. The experimental group were given oral treatments included compound 2-4 at the dosages of 25, 50 and 100 mg/kg body weight, respectively, using an everyday 30 times (dosing regimen: QD×30, p.o.); whereas control group were given orally with 30 μL of DMSO throughout the experimental period. The tumor size (mm$^3$) from each mouse was determined utilizing a caliper by calculating as 0.5×length×(width)$^2$. At the end of treatment, all animals were anaesthetized by carbon dioxide ($CO_2$) and sacrificed on 31$^{st}$ day. The tumor tissues from each mouse were removed then measured and weighed individually as previously reported.

Biochemical Analysis—the Levels of Biochemical Enzyme Profiles and Hematologic Counts All mice were monitored the relative toxicity of each group after the animals were sacrificed, and whole blood samples were drawn from the heart for biochemical measurements to evaluate the safety of compound 2-4. Briefly, blood was collected from each mouse and allowed to clot and centrifuged at 1000×g for 10 minutes at room temperature for further biochemical tests including total protein, albumin, creatinine, blood urea nitrogen (BUN), uric acid and glucose.

Example 17

Antiproliferation Effect of Compounds of the Invention on Hep3B Cells and CAR Cells Please refer to Table 1. Hep3B cells and CAR cells were treated by different concentrations of the compounds of the invention for 48 and 72 hours, and the antiproliferation effect of such compounds was evaluated using MTT assay. Data are presented as IC$_{50}$ (μM), the concentration of 50% proliferation-inhibitory effect.

TABLE 1

| Compound | Structure | Hep 3B (IC$_{50}$ (μM)) | | CAR (IC$_{50}$ (μM)) | |
| --- | --- | --- | --- | --- | --- |
| | | 48 hours | 72 hours | 48 hours | 72 hours |
| Compound 2-4 Molecular Weight: 372.41 | 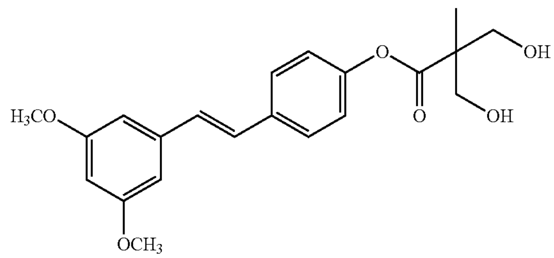 [SMILES: COc1cc(/C=C/c2ccc(OC(=O)C(C)(CO)CO)cc2)cc(OC)c1] | 63.51 | 43.83 | 73.00 | 45.16 |
| Compound 3-5 Molecular Weight: 344.35 | 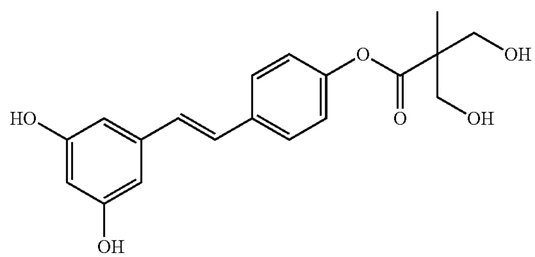 [SMILES: CC(CO)(CO)C(=O)Oc1ccc(/C=C/c2cc(O)cc(O)c2)cc1] | 144.05 | 47.83 | 168.56 | 132.68 |
| Compound 3-6 Molecular Weight: 460.47 | 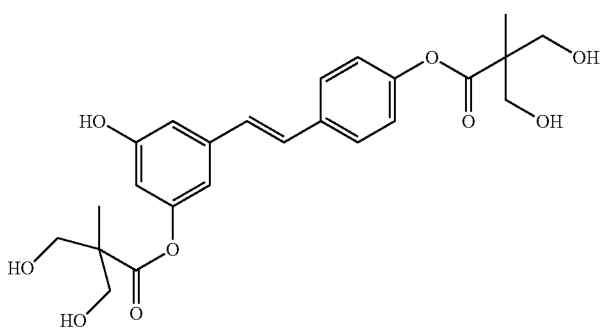 [SMILES: CC(CO)(CO)C(=O)Oc1ccc(/C=C/c2cc(O)cc(OC(=O)C(C)(CO)CO)c2)cc1] | 54.21 | 36.77 | 105.20 | 113.30 |
| Compound 4-3 Molecular Weight: 576.58 | 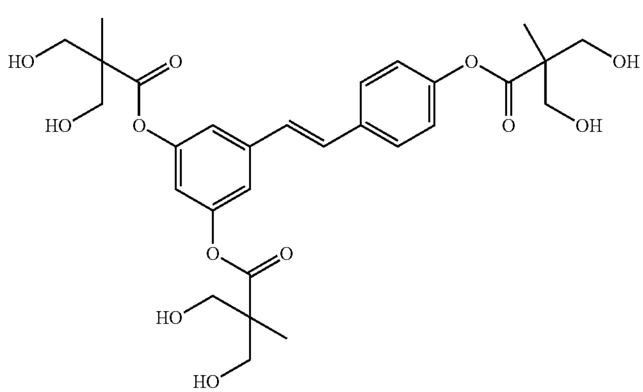 [SMILES: CC(CO)(CO)C(=O)Oc1ccc(/C=C/c2cc(OC(=O)C(C)(CO)CO)cc(OC(=O)C(C)(CO)CO)c2)cc1] | 150.91 | 95.04 | 149.01 | 124.05 |

TABLE 1-continued

| Compound | Structure | Hep 3B (IC$_{50}$ (μM)) | | CAR (IC$_{50}$ (μM)) | |
| --- | --- | --- | --- | --- | --- |
| | | 48 hours | 72 hours | 48 hours | 72 hours |
| Compound 6-3 Molecular Weight: 460.47 | 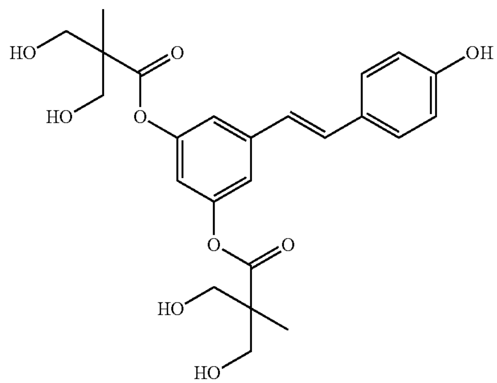 [SMILES: CC(CO)(CO)C(=O)Oc1cc(/C=C/c2ccc(O)cc2)cc(OC(=O)C(C)(CO)CO)c1] | 136.76 | 55.28 | 91.41 | 76.99 |
| Compound 5-3 Molecular Weight: 344.35 | 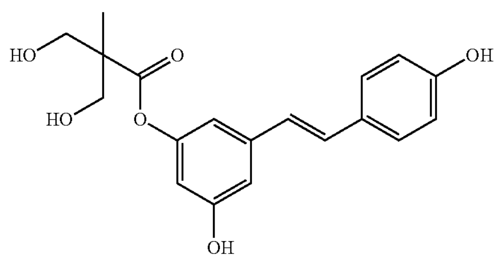 [SMILES: CC(CO)(CO)C(=O)Oc1cc(O)cc(/C=C/c2ccc(O)cc2)c1] | 83.54 | 68.86 | 54.90 | 113.46 |
| Compound 7-3 Molecular Weight: 372.41 | 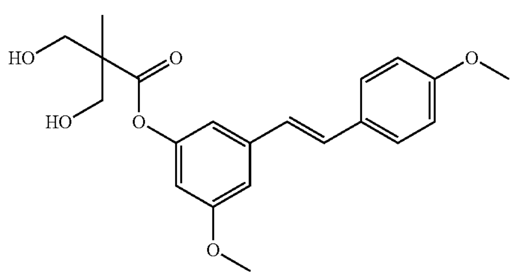 [SMILES: COc1ccc(/C=C/c2cc(OC)cc(OC(=O)C(C)(CO)CO)c2)cc1] | 70.78 | 48.71 | 64.17 | 67.32 |
| Compound 8-3 Molecular Weight: 474.5003 | 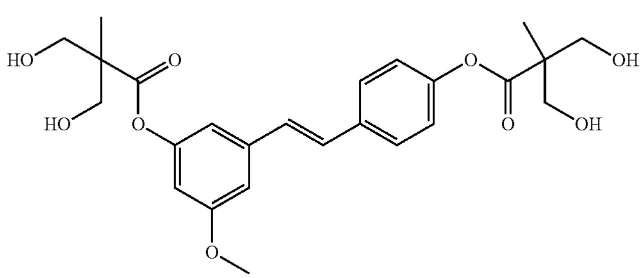 [SMILES: COc1cc(/C=C/c2ccc(OC(=O)C(C)(CO)CO)cc2)cc(OC(=O)C(C)(CO)CO)c1] | 106.41 | 66.48 | 56.45 | 59.81 |
| Compound 9-4 Molecular Weight: 428.43 | 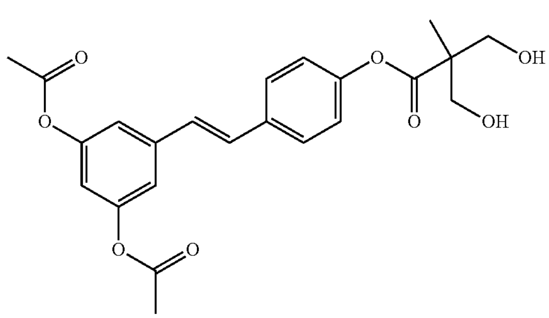 [SMILES: CC(=O)Oc1cc(/C=C/c2ccc(OC(=O)C(C)(CO)CO)cc2)cc(OC(C)=O)c1] | 147.74 | 62.01 | 103.21 | 115.76 |

TABLE 1-continued
| Compound | Structure | Hep 3B (IC$_{50}$ (μM)) 48 hours | Hep 3B (IC$_{50}$ (μM)) 72 hours | CAR (IC$_{50}$ (μM)) 48 hours | CAR (IC$_{50}$ (μM)) 72 hours |
|---|---|---|---|---|---|
| Compound 10-4 Molecular Weight: 502.51 | 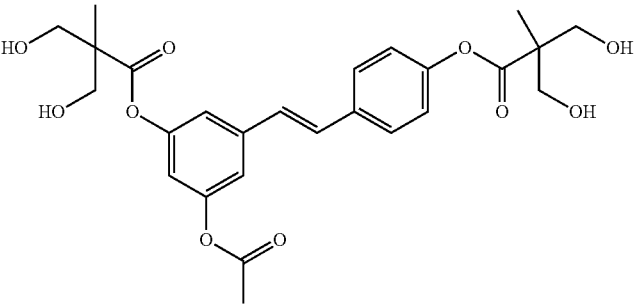 [SMILES: CC(=O)Oc1cc(/C=C/c2ccc(OC(=O)C(C)(CO)CO)cc2)cc(OC(=O)C(C)(CO)CO)c1] | >200 | >200 | 122.14 | 119.28 |
| Compound 11-3 Molecular Weight: 358.38 | 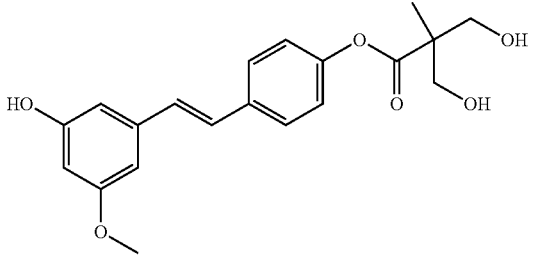 [SMILES: COc1cc(O)cc(/C=C/c2ccc(OC(=O)C(C)(CO)CO)cc2)c1] | 88.94 | 33.24 | 67.31 | 63.96 |
| Compound 12-3 Molecular Weight: 400.4218 | 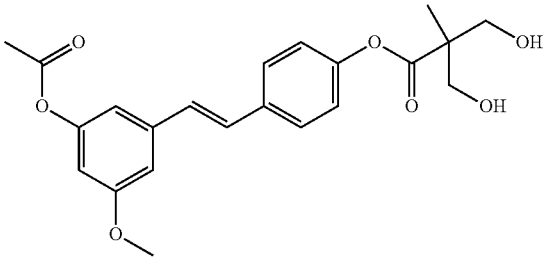 [SMILES: COc1cc(/C=C/c2ccc(OC(=O)C(C)(CO)CO)cc2)cc(OC(C)=O)c1] | 85.21 | 36.81 | 51.99 | 50.30 |
| Compound 13-3 Molecular Weight: 474.50 | 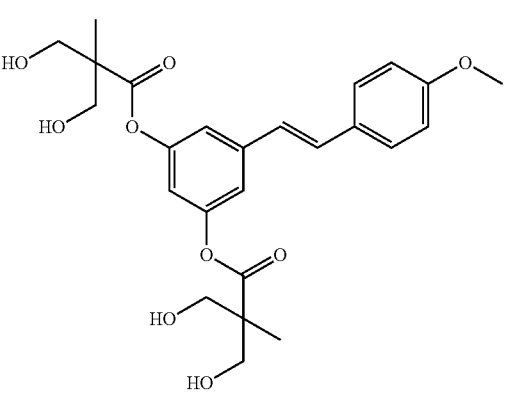 [SMILES: COc1ccc(/C=C/c2cc(OC(=O)C(C)(CO)CO)cc(OC(=O)C(C)(CO)CO)c2)cc1] | 53.39 | 39.11 | 73.93 | 70.75 |

TABLE 1-continued

| Compound | Structure | Hep 3B (IC$_{50}$ (μM)) | | CAR (IC$_{50}$ (μM)) | |
| --- | --- | --- | --- | --- | --- |
| | | 48 hours | 72 hours | 48 hours | 72 hours |
| Compound 14-5 Molecular Weight: 484.5382 | 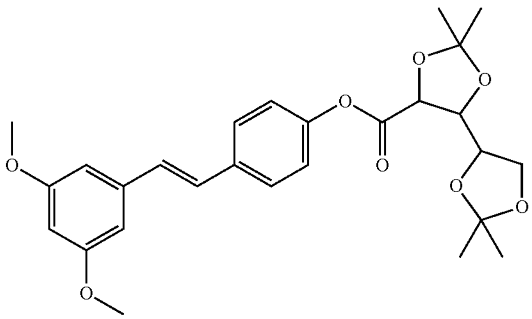 [SMILES: COc1cc(/C=C/c2ccc(OC(=O)C3OC(C)(C)OC3C3COC(C)(C)O3)cc2)cc(OC)c1] | 94.68 | 59.49 | >200 | >200 |
| Pterostilbene Molecular Weight: 256.29 | 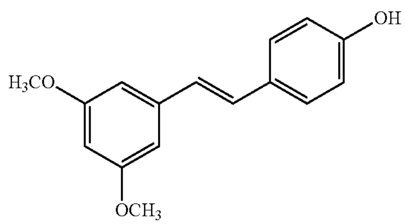 [SMILES: COc1cc(/C=C/c2ccc(O)cc2)cc(OC)c1] | 75.33 | 48.94 | 100.34 | 98.29 |
| Resveratrol Molecular Weight: 228.24 | 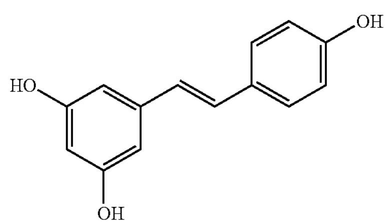 [SMILES: Oc1ccc(/C=C/c2cc(O)cc(O)c2)cc1] | 96.42 | 51.61 | 152.67 | 88.26 |

As shown in Table 1, all the tested compounds show significant activities against Hep 3B and CAR cells. Among them, compound 2-4, 3-6, 7-3, 11-3, 12-3, and 13-3 show more potent anticancer activity than resveratrol and pterostilbene.

Example 18

Antiproliferation of Compound 2-4 Against Cisplatin-Resistant Head and Neck Squamous Carcinoma (CAR) Cell MTT assay was utilized and CAR cells were treated with compound 2-4 in different concentration for 24, 48 and 72 hours. The result is shown in FIG. 1, which indicated that compound 2-4 demonstrated concentration- and time-dependent antiproliferative effect on CAR cells. The IC$_{50}$ after 72 hours of treatment was 50 μM.

Example 19

Antiproliferation of Compound 24 Against Hep3B Cells

Figure 2:
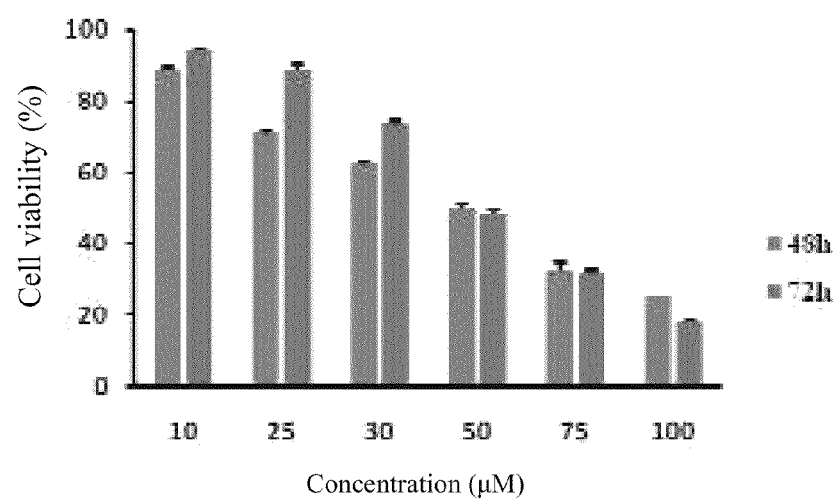
FIG. 2, effect of compound 2-4 on viability of Hep3B hepatoma cells.

The anti-proliferative ability of compound 2-4 in hepatocellular carcinoma was evaluated in Hep3B cells using MTT assay. Hep3B cells were treated with various concentrations of compound 2-4 for 48 and 72 hours. As shown in FIG. 2, compound 2-4 displayed an effectively concentration-dependent inhibition on cell viability in Hep3B cells. The IC$_{50}$ after 48 hours of treatment was 50 μM. The result shown in FIG. 2 indicates that compound 2-4 do exhibit a potent inhibitory effect in hepatocellular carcinoma.

Example 20

In Vivo Antitumor Activity of Compound 2-4

Figure 3:
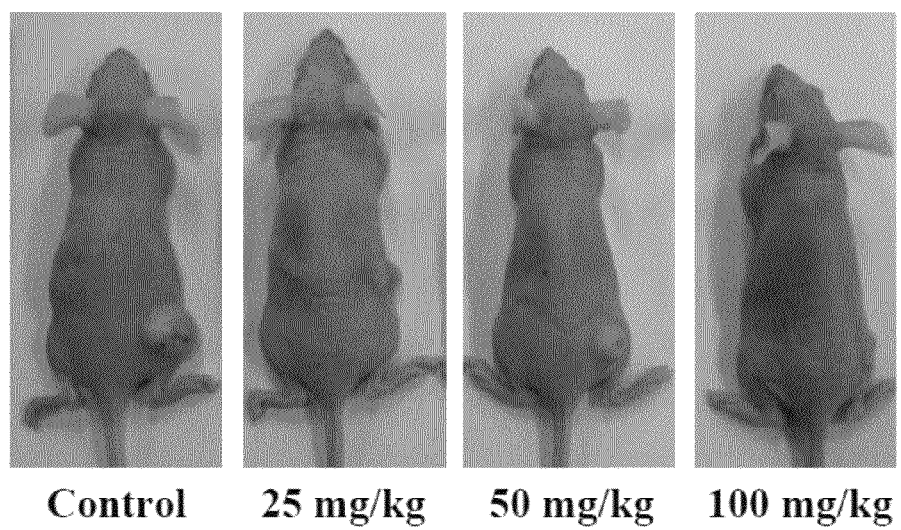
FIG. 3, effect of compound 2-4 in CAR xenograft nude mice model.
Figure 4:
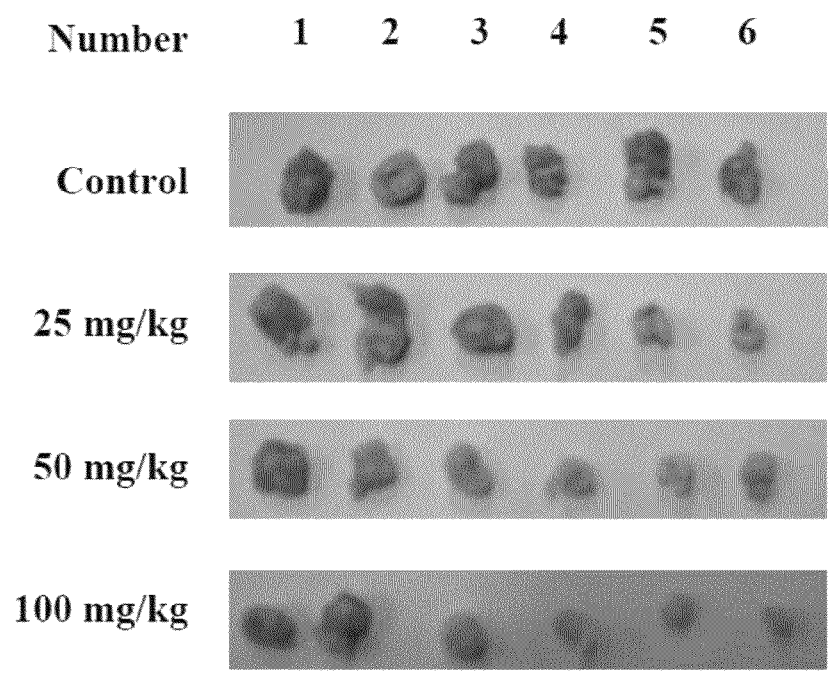
FIG. 4, effect of compound 2-4 on tumor size in CAR xenograft nude mice model.
Figure 5:
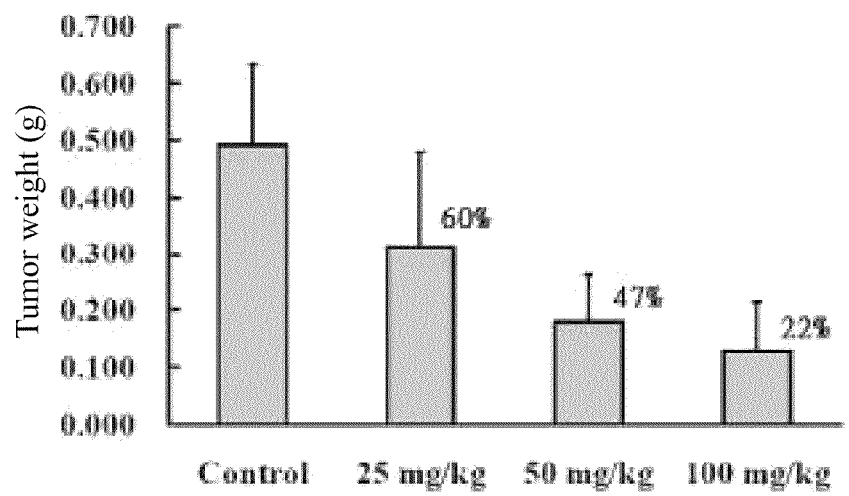
FIG. 5, effect of compound 2-4 on tumor weight in CAR xenograft nude mice model.

Compound 2-4 was evaluated in the CAR xenograft nude mice by oral route (p.o.) at dose of 25, 50, and 100 mg/kg/day in a schedule of QD×30. Based on the results shown in FIGS. 3, 4 and 5, compound 2-4 exhibits dose-dependent inhibitory effect on CAR tumor size (FIGS. 3 and 4), and tumor weight (FIG. 5). Significant tumor growth suppression was also observed at the dose of 25 mg/kg/day. At the 100 mg/kg/day dose of compound 2-4, the weight of CAR tumor was reduced down to 22% that of the vehicle control (FIG. 5).

Figure 6:
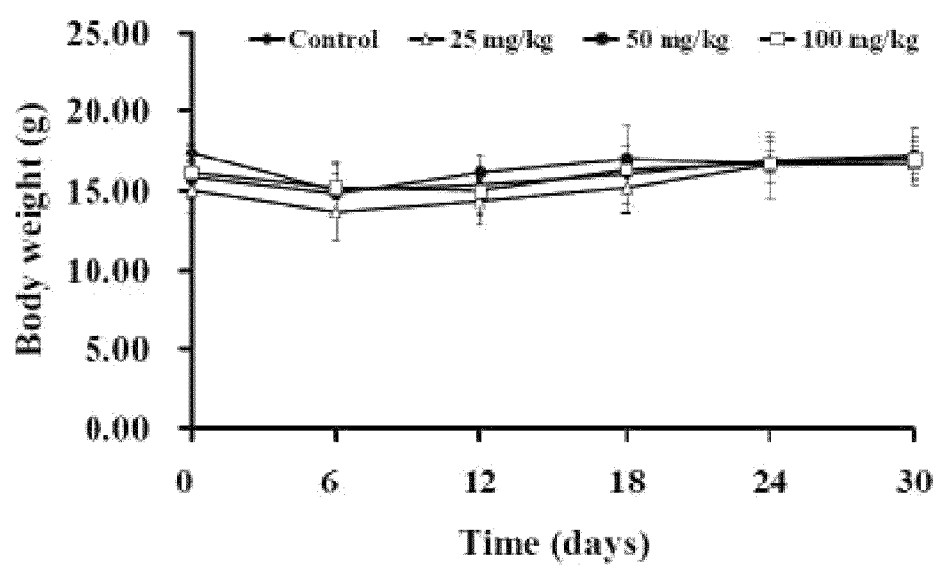
FIG. 6, mean body weight-time profile of compound 2-4 in CAR xenograft nude mice model.

During the antitumor evaluation of compound 2-4, no significant body weight change was detected in either the mice treated by compound 2-4 or the control mice (FIG. 6). Furthermore, after 30 days of treatment, these mice were sacrificed and their blood samples were collected for biochemical quantification of total protein, albumin, creatinine, blood urea nitrogen, uric acid and glucose. According to the blood analysis result summarized in Table 2, no significant difference in blood analysis result was observed between the blood of mice treated by compound 2-4 and the vehicle control mice. Compound 2-4 displays significant antitumor activity with very low toxicity when orally administered.

TABLE 2

| Group | Total Protein (g/dL) | Albumin (g/dL) | Blood urea nitrogen (mg/dL) | Creatinine (mg/dL) | Uric acid (mg/dL) | Glucose (mg/dL) |
|---|---|---|---|---|---|---|
| Control | 5.600 ± 0.283 | 3.450 ± 0.138 | 27.700 ± 4.116 | 1.000 ± 0.180 | 4.650 ± 0.864 | 180.000 ± 10.392 |
| 25 mg/kg | 5.383 ± 0.117 | 3.666 ± 0.052 | 28.200 ± 5.784 | 1.133 ± 0.109 | 4.567 ± 0.784 | 181.333 ± 32.067 |
| 50 mg/kg | 5.583 ± 0.376 | 3.417 ± 0.075 | 30.950 ± 1.265 | 0.910 ± 0.077 | 5.450 ± 0.878 | 172.500 ± 6.504 |
| 100 mg/kg | 5.283 ± 0.194 | 3.400 ± 0.089 | 29.250 ± 3.855 | 0.830 ± 0.128 | 5.050 ± 1.882 | 196.500 ± 8.643 |

Results were performed as mean ± S.E.M. at least five samples from each group.

Example 21

Effect of Compound 2-4 on Normal Oral Cells

Human normal gingival fibroblasts cells (HGF) and human normal oral keratinocyte cells (OK) were acquired from Department of Dental Hygiene, China Medical University, Taiwan. HGF and OK were cultivated in DMEM.

Both HGF and OK cells ($1 \times 10^4$ cells) were placed into a 96-well plate and were incubated with 0, 25, 50 and 100 µM of compound 2-4 for 24, 48 and 72 hours. For incubation with the autophagy inhibitor, cells were pretreated with 3-methylamphetamine (3-MA, 10 mM) for 1 hour, followed by treatment with or without compound 2-4 (50 and 75 µM) for 48 hours. After washing the cells, DMEM containing MTT (0.5 mg/mL) was added to detect viability. The cell viability was expressed as % of the control.

Figure 7:
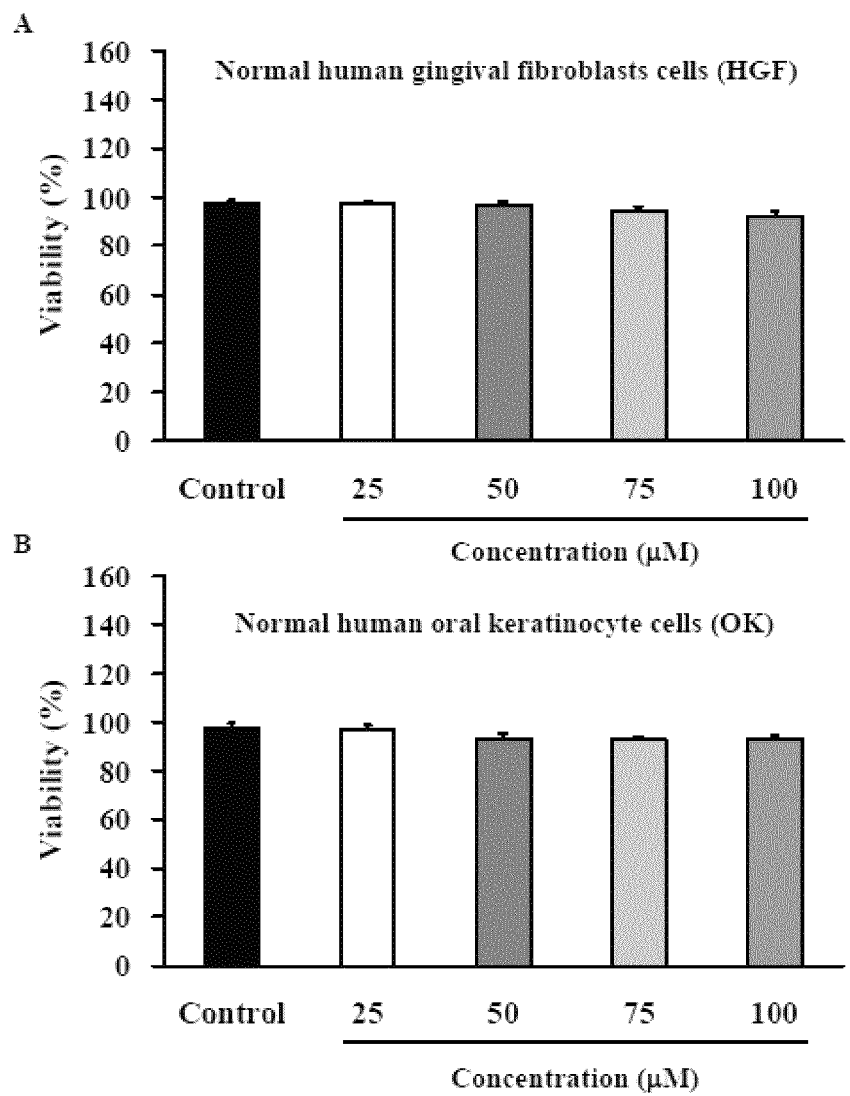
FIG. 7, effect of compound 2-4 on normal oral cells.

The result of effect of compound 2-4 on normal oral cells, HGF and OK, is shown in FIG. 7. In FIG. 7, (A) indicates HGF cells and (B) indicates OK cells after exposure to various concentrations of compound 2-4 for 72 hours. The cell viability is determined by MTT assay and the data shown represent the mean±S.E.M (n=3). As shown in FIG. 7, for both HGF and OK cells, no viability impact is observed when treated with compound 2-4, indicating that compound 2-4 has an extremely low toxicity in normal oral cells, HGF and OK; thus, is completely safe to be used on normal cells.

Example 22

Water Solubility Assay of the Compounds of the Present Invention

The water solubility of the compounds of the present invention can be determined by methods known in the art and the result is shown in Table 3.

TABLE 3

| Compound | Content (µg/mL) |
|---|---|
| Compound 3-5 | 52.9 |
| Compound 3-6 | 135.7 |
| Compound 4-3 | 372.4 |
| Compound 5-3 | 409.6 |
| Compound 6-3 | 454.8 |
| Compound 7-3 | 53.4 |
| Compound 8-3 | >1000 |
| Compound 9-4 | 306.2 |
| Compound 10-4 | >1000 |
| Compound 11-3 | 35.8 |
| Compound 12-3 | 81.9 |
| Compound 13-3 | 336.7 |
| Compound 14-5 | <10 |
| Compound 2-4 | 18.0 |
| Pterostilbene | 48.0 |
| Resveratrol | 107.2 |

The water solubility assay results suggested the Compounds 3-6, 4-3, 5-3, 6-3, 8-3, 9-4 and 10-4 increased water solubility 1 to 12 times when compared with resveratrol. The results also indicated that the introduction of 3-hydroxy-2-(hydroxymethyl)-2-methylpropanoic acid into pterostilbene improve water solubility 1 to 28 times.

The compounds and the pharmaceutical composition as well as uses thereof provided herein are applicable and valuable to the industry. Those embodiments above are better results, and should not, however, be considered to limit the scope of the invention. It is contemplated that modifications will readily occur to those skilled in the art, which modifications will be within the spirit of the invention and scope of the appended claims.

What is claimed is:

1. A compound of Formula I:

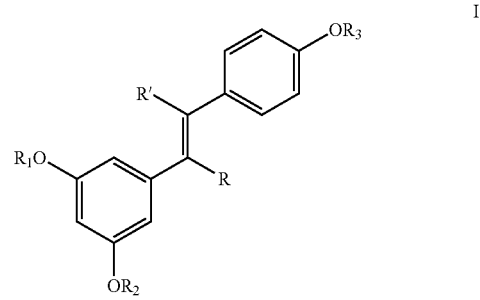

or a stereoisomer, a geometric isomer, a tautomer, an N-oxide, a hydrate, a solvate, a prodrug, or a pharmaceutically acceptable salt thereof, wherein R', R is hydrogen or $C_{1-3}$ alkyl; $R_1$, $R_2$, $R_3$ are each, independently, hydrogen, $C_{1-3}$ alkyl,

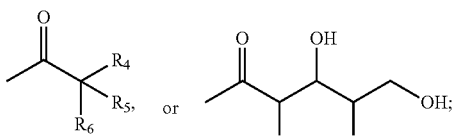

and at least one of $R_1$, $R_2$, $R_3$ is

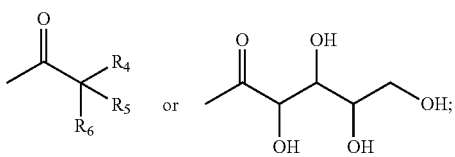

$R_4$, $R_5$, $R_6$ are each, independently, hydrogen, $C_{1-3}$ alkyl, $(CH_2)_n$—$CH_2OH$, or $(CHOH)_n$—$CH_2OH$, wherein n=0 to 3; and at least one of $R_4$, $R_5$, $R_6$ is $(CH_2)_n$—$CH_2OH$ or $(CHOH)_n$—$CH_2OH$, wherein n=0 to 3.

2. The compound of claim 1, wherein when $R_1$, $R_2$, $R_3$ are each, independently,

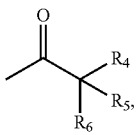

at least one of $R_4$, $R_5$, $R_6$ is $(CH_2)_n$—$CH_2OH$, wherein n=0 to 3.

3. The compound of claim 1, wherein when $R_1$, $R_2$, $R_3$ are each, independently,

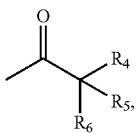

at least one of $R_4$, $R_5$, $R_6$ is $(CHOH)_n$—$CH_2OH$, wherein n=0 to 3.

4. A pharmaceutical composition comprising the compound of claim 1.

5. The pharmaceutical composition of claim 4 further comprising a pharmaceutically acceptable carrier, excipient, diluent, adjuvant, medium, or combinations thereof.

6. A method of treating squamous carcinoma/hepatoma in a subject in need thereof, the method comprising administrating to the subject an therapeutically effective amount of the compound of claim 1.

7. A compound of Formula II:

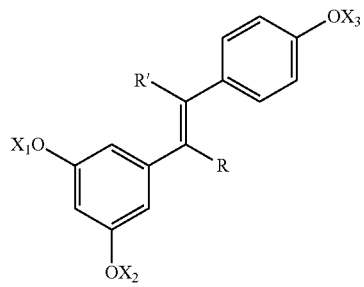

wherein, R', R is hydrogen or $C_{1-3}$ alkyl; $X_l$, $X_2$, $X_3$ are each, independently, hydrogen, $C_{1-3}$ alkyl, or

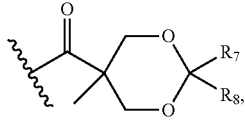

wherein $R_7$ and $R_8$ are each, independently, hydrogen or $C_{1-3}$ alkyl; and at least one of $X_1$, $X_2$, $X_3$ is

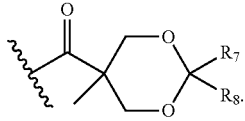

* * * * *